United States Patent
Godec et al.

[11] Patent Number: 5,798,271
[45] Date of Patent: Aug. 25, 1998

[54] APPARATUS FOR THE MEASUREMENT OF DISSOLVED CARBON IN DEIONIZED WATER

[75] Inventors: Richard D. Godec, Longmont; Kevin J. O'Neill, Boulder; Paul K. Kosenka, Denver, all of Colo.

[73] Assignee: Sievers Instruments, Inc., Boulder, Colo.

[21] Appl. No.: 629,033

[22] Filed: Apr. 8, 1996

Related U.S. Application Data

[63] Continuation-in-part of Ser. No. 501,597, Jul. 12, 1995, which is a continuation-in-part of Ser. No. 869,308, Apr. 16, 1992, Pat. No. 5,443,991, which is a division of Ser. No. 487,720, Mar. 2, 1990, Pat. No. 5,132,094.

[51] Int. Cl.$^6$ .................................................. G01N 25/18
[52] U.S. Cl. .................. 436/146; 436/145; 436/150; 436/155; 436/158; 422/78; 422/80; 422/82.02; 422/90; 422/93
[58] Field of Search .............. 422/78, 80, 82.02, 422/90, 93; 436/145, 146, 150, 155, 158

[56] References Cited

U.S. PATENT DOCUMENTS

| | | | |
|---|---|---|---|
| 3,224,837 | 12/1965 | Moyat | 23/230 |
| 3,958,941 | 5/1976 | Regan | 23/253 |
| 4,209,299 | 6/1980 | Carlson | 23/230 |
| 4,273,558 | 6/1981 | Mar | 23/230 PC |
| 4,277,438 | 7/1981 | Ejzak | 422/80 |
| 4,288,229 | 9/1981 | Mar | 23/230 |
| 4,293,522 | 10/1981 | Winkler | 422/80 |
| 4,352,673 | 10/1982 | Espitalie et al. | 422/80 |
| 4,504,373 | 3/1985 | Mani et al. | 204/180 |
| 4,519,983 | 5/1985 | Espitalie et al. | 436/145 |
| 4,529,495 | 7/1985 | Marsoner | 204/411 |
| 4,619,902 | 10/1986 | Bernard | 436/145 |
| 4,626,413 | 12/1986 | Blades et al. | 422/78 |
| 4,666,860 | 5/1987 | Blades et al. | 436/146 |
| 4,749,657 | 6/1988 | Takahashi et al. | 436/146 |
| 4,775,634 | 10/1988 | Sienkiewicz | 436/146 |
| 4,868,127 | 9/1989 | Blades et al. | 436/146 |
| 5,047,212 | 9/1991 | Blades et al. | 422/82 |
| 5,132,094 | 7/1992 | Godec et al. | 422/68 |
| 5,141,717 | 8/1992 | McRae | 422/82 |
| 5,312,756 | 5/1994 | Jolly | 436/8 |
| 5,443,991 | 8/1995 | Godec et al. | 436/145 |

*Primary Examiner*—Jill Warden
*Assistant Examiner*—Sharidan Carrillo
*Attorney, Agent, or Firm*—Lappin & Kusmer, LLP

[57] ABSTRACT

Apparatus and methods for the measurement of total organic carbon, total inorganic carbon, total carbon and total heteroorganic carbon of deionized water are described. In a preferred embodiment, the sample is split into a first stream and a second stream. Inorganic carbon in the first stream is measured using a temperature and conductivity cell, and then the organic carbon in the first stream is oxidized in a U.V. oxidation module. The resulting carbon dioxide is transferred through a carbon dioxide permeable membrane into the second stream. The second stream then passes into a second temperature and conductivity cell for the measurement of total carbon.

53 Claims, 8 Drawing Sheets

APPARATUS FOR THE MEASUREMENT OF DISSOLVED CARBON IN DEIONIZED WATER

CROSS REFERENCE TO RELATED APPLICATIONS

This application is a continuation-in-part of U.S. patent application Ser. No. 08/501,597, filed Jul. 12, 1995, now pending, which in turn was a continuation-in-part of U.S. patent application Ser. No. 07/869,308, filed Apr. 16, 1992, now U.S. Pat. No. 5,443,991 issued Aug. 22, 1995, which in turn was a division of U.S. patent application Ser. No. 07/487,720, filed Mar. 2, 1990, now U.S. Pat. No. 5,132,094 issued Jul. 21, 1992.

BACKGROUND OF THE INVENTION

1. Technical Field

The present invention relates to an improved method and apparatus for the determination of the total concentration of organic carbon compounds in aqueous process streams and in bulk solutions. The invention is especially adapted for use in measuring carbon in deionized water or deionized water with dissolved carbon dioxide, which is often used in the manufacture and processing of electronic components, fine chemicals and pharmaceuticals. Particularly, the method of the present invention in a preferred embodiment includes the measurement of the temperature and conductivity of an aqueous sample, the oxidation of the organic components of the sample stream, and the sensitive and selective detection of carbon dioxide utilizing a selective carbon dioxide gas permeable membrane and conductometric detection to determine the level of organic carbon in the sample.

2. Background Art

The measurement of the total organic carbon (TOC) concentration and total carbon (organic plus inorganic) concentration in water has become a standard method for accessing the level of contamination of organic compounds in potable waters, industrial process waters, and municipal and industrial waste waters. In addition to widespread terrestrial applications, the measurement of TOC is one of the primary means of determining the purity of potable and process waters for manned space-based systems including the space shuttle, the proposed space station and for future manned explorations of the moon and planets.

The United States Environmental Protection Agency recently promulgated new rules aimed at reducing the levels of disinfectant by-products in drinking water. Formed from the reaction of chlorine and other disinfectants with naturally occurring organic matter, disinfectant by-products are potentially hazardous compounds including trihalomethanes ($CHCl_3$, $CHBrCl_2$, etc.), haloacetic acids, and other halogenated organic species. The new rules also require monitoring the levels of natural organic material in raw water, during the treatment process and in the finished water by measurement of total organic carbon concentration.

Very pure water is used for the manufacture of electronic components, and also in certain processes involving fine chemicals and pharmaceuticals. The water required for such uses is often deionized and carbon based impurity concentration in the parts per billion or even parts per trillion range must be monitored.

A variety of prior art approaches for measuring the total organic carbon content of water have been proposed. For example, See U.S. Pat. Nos. 3,958,941 of Regan; 3,224,837 of Moyat; 4,293,522 of Winller; 4,277,438 of Ejzak; 4,626,413 of Blades, et al. and 4,666,860 of Blades, et al.; and 4,619,902 of Bernard.

Representative of the devices described in these references are the methods disclosed in U.S. Pat. No. 3,958,941 of Regan. In Regan an aqueous sample is introduced into a circulating water stream that flows through a reaction chamber where the sample is mixed with air and exposed to ultraviolet (U.V.) radiation to promote the oxidation of organic compounds found in the sample to form carbon dioxide. The carbon dioxide formed in the reaction chamber is then removed from solution by an air stripping system and introduced into a second chamber containing water that has been purified to remove ionic compounds. The conductivity of the water in the second chamber is measured, and any increase in conductivity is related to the total concentration of carbon dioxide following oxidation in the first reactor. The conduction measurement can be used, therefore, to determine the concentration of total carbon in the original sample. If the level of inorganic carbon is known, or inorganic carbon compounds are removed prior to evaluation, the concentration of organic carbon can be determined.

The Regan device is slow, cannot be used for the continuous monitoring of TOC concentration in aqueous streams, cannot be scaled down without increasing interference from $NO_2$, $SO_2$, and $H_2S$ to unacceptable levels, and is generally unsatisfactory. In any system that requires the removal of carbon dioxide from an aqueous solution by air stripping, the pH of the solution must be reduced to a 4.0 or less to ensure that all of the carbon is in the form of carbon dioxide. The Regan patent does not teach that acid must be added to the sample stream to achieve this requirement. The oxidation method disclosed by Regan is unsatisfactory for the measurement of refractory compounds, particularly urea.

In Regan, an aqueous sample of 20 to 100 mL containing 0.5 mg/L organic carbon is required to generate sufficient carbon dioxide for accurate detection, thus limiting the utility of the device for the measurement of parts per million levels or lower of TOC in smaller sample sizes. Finally, in practice, the Regan system requires frequent recalibration—typically once per day—due to variations in background conductivity. Also, the concentration of total organic carbon in the calibration standard must be approximately equal to the concentration of organic carbon in the sample. Because of this, recalibration is required when analyzing aqueous samples containing higher or lower levels of organic carbon when compared with the calibration standard.

An improved method and apparatus for the measurement of organic content of aqueous samples is disclosed in U.S. Pat. No. 4,277,438 of Ejzak. Ejzak describes a multistage reactor design which provides for the addition of oxygen and a chemical oxidizing agent, preferably sodium persulfate, to an aqueous sample stream prior to oxidation of the stream using ultraviolet radiation in a series of reactors. Ejzak also describes the use of an inorganic carbon stripping process—before oxidation of the organic carbon—that includes the addition of phosphoric acid to the sample stream. After oxidation, the sample stream is passed into a gas-liquid separator where the added oxygen acts as a carrier gas to strip carbon dioxide and other gases from the aqueous solution. In the preferred embodiment, the gas stream is then passed through an acid mist eliminator, a coalescer and salt collector, and through a particle filter prior to passage into an infrared (IR) detector for the measurement of the concentration of carbon dioxide in the gas stream.

The methods and apparatus disclosed by Ejzak provide improvements over the teachings of Regan; however, the Ejzak device requires extensive manual operation and is also generally unsatisfactory. The Ejzak device requires three external chemical reagents; oxygen gas, aqueous phosphoric acid and an aqueous solution of sodium persulfate. Both the phosphoric acid and persulfate solutions must be prepared at frequent intervals by the operator due to the relatively high rate of consumption. The Ejzak device requires dilution of the sample if the solution contains high concentrations of salts in order to ensure complete oxidation of the sample and to eliminate fouling of the particle filter located prior to the IR carbon dioxide detector. As with Regan, relatively large sample sizes are required—typically 20 mL of sample for accurate measurement at 0.5 mg/L total organic carbon—and the carbon dioxide formed in the oxidation chamber is removed using a gravity dependent technique that cannot be easily used in space-based operations.

Another improved method and apparatus for the measurement of total organic carbon in water is disclosed in U.S. Pat. No. 4,293,522 of Winkler. In Winkler, an oxidizing agent, molecular oxygen, is generated in-situ by the electrolysis of water. Organic compounds are subsequently oxidized to form carbon dioxide by the use of U.V. radiation and the in-situ generated oxygen. The irradiation and electrolysis processes are both accomplished in a single oxidation chamber. Winkler does not teach that the aqueous sample stream be acidified to assist in the removal of carbon dioxide from solution, and in fact teaches against the use of acid. Therefore, this method and apparatus cannot be used for the measurement of organic compounds in basic aqueous samples. The oxidation chamber of Winkler uses a solid electrolyte to separate the two electrodes employed for the electrolysis of water. The solid electrolyte described by Winkler is composed of an organic polymer which, upon exposure to oxygen, ozone and U.V. radiation, will undergo limited oxidation to form carbon dioxide, therefore resulting in unacceptable background levels of organic compounds in the sample stream, particularly at low organic compound concentrations.

The Winkler patent describes a conductometric carbon dioxide detection system wherein the sample stream exiting the oxidization chamber is maintained in an equilibrating relationship with a stream of deionized water. The two flowing streams are separated by a gas permeable membrane, a microporous teflon (Gore-tex), that permits the concentration of carbon dioxide to equilibrate between the streams. The concentration of the carbon dioxide generated in the oxidation chamber is thereafter determined by measuring the conductance of the deionized water stream. However, the use of two continuously flowing and recirculating streams with separate pumps on either side of the membrane as taught by Winkler introduces precise operating parameters into the detection process that require frequent calibration adjustments, such as adjustments necessitated by ionic contamination from the circulatory pump. Using one pump for the sample stream and a different pump for the deionized water stream can produce varying differential flow rates which introduce additional errors into the system. The use of a microporous teflon membrane as taught in the Winkler patent allows the passage of acid gases other than carbon dioxide, thereby interfering with the measurement of carbon dioxide. The device described in Winkler uses a large volume batch process which would also be very time-consuming to operate, to the point where it would not be practical for commercial use.

Another TOC detector of the prior art is disclosed in U.S. Pat. No. 4,619,902 of Bernard, which teaches the oxidation of organic compounds to form carbon dioxide using persulfate oxidation at elevated temperatures—typically 20° to 100° C. in the presence of a platinum metal catalyst. Bernard recognizes that the materials used in the construction of instrumentation for the determination of total organic carbon in water can contribute organic compounds to the sample during the measurement process, and teaches that inert materials such as PTFE must be used to reduce this background from the measurement. As with certain of the previously mentioned disclosures, a gas stripping technique is employed to collect the formed carbon dioxide, and measurement is made using IR spectrometry. Bernard also recognizes that aqueous solutions of sodium persulfate are relatively instable due to auto-degradation of the reagent.

An additional system for the measurement of organic compounds in deionized water is disclosed in U.S. Pat. No. 4,626,413 of Blades and Godec. The apparatus described by Blades and Godec utilizes direct U.V. oxidation of organic compounds to form carbon dioxide, which is measured by using conductometric detection during the oxidation process. In the apparatus and method described in the Blades and Godec patent, the oxidation of some organic compounds containing halogens and other hetero atoms will lead to the formation of strong acids such as HCl, $H_2SO_4$ and $HNO_3$, which interfere with the conductometric method employed. The TOC detector described in the Blades and Godec patent operates in a batch mode where the oxidation can be unpredictable and can be very long (greater than 25 minutes). This does not allow this device to be an effective real time analyzer. The sample chamber in the device is relatively large, and large amounts of sample must be flushed through the chamber between evaluations, and is therefore difficult to calibrate using normal chemical standards. The Blades device is also limited to the measurement of total organic compounds in deionized water and cannot be used for samples containing ionic compounds other than bicarbonate ion.

In U.S. Pat. No. 4,209,299 of Carlson, it is disclosed that the concentration of volatile materials in a liquid can be quantitatively determined by transferring the desired material through a gas permeable membrane into a liquid of known conductivity, such as deionized water. The Carlson patent describes the measurement of a number of volatile organic and inorganic compounds, but does not suggest the combination of the method or process in conjunction with a carbon dioxide producing reactor. The Carlson patent does not teach the use of a selective membrane to limit the measurement to the gas of interest.

An improved carbon analyzer is disclosed in related U.S. Pat. No. 5,132,094 by Godec et al. (See also, related U.S. Pat. No. 5,443,991.) The Godec patents are commonly assigned with the present invention, and are herein incorporated in their entirety by this reference. Originally developed for NASA, the device described in the Godec patents uses UV/persulfate oxidation and a novel $CO_2$ detection technique utilizing a selective gas-permeable membrane and a conductivity cell. The gas-permeable membrane is used to separate the acidified sample stream (pH<2) from a thin layer of deionized water. A solenoid valve is opened to allow fresh deionized water to flow into the membrane module and the solenoid valve is closed. Carbon dioxide formed from the oxidation of organic compounds will selectively diffuse across the membrane into the deionized water, where a portion of the $CO_2$ will ionize to produce $H^+$ and $HCO_3^-$ ions. After an equilibration period, the solenoid valve is opened to flush the solution into a conductivity and temperature measurement cell, and the concentration of $CO_2$ in the deionized water is determined from the conductivity and temperature measurements.

The selective membrane-based conductivity detection of carbon dioxide in a TOC detector as taught in the Godec patent offers several advantages to other methods. Calibration is extremely stable, and the calibration can be easily performed by the analyst. No purge gases are required. The technique is highly selective for carbon dioxide because of the use of a selective carbon dioxide gas permeable membrane which is extremely sensitive, permitting detection of TOC down to parts per trillion levels. It also has a wide dynamic range, permitting measurement of up to at least 50 ppm TOC without sample dilution.

In operation of one of the preferred embodiments taught in the Godec patent, the sample is drawn into an analyzer by means of a peristaltic pump, and two reagents are added via syringe pumps. Acid (6M $H_3PO_4$) is added to reduce the pH of the sample stream and ammonium persulfate (15% $(NH_4)_2S_2O_8$) is added to assist in the oxidation of organic compounds in the sample stream. The sample stream is split for measurement of inorganic carbon (IC) concentration (IC= $[HCO_3{-}]+[CO_3{-}^2]+[CO_2]$) without oxidation, and the measurement of total carbon (TC) concentration after oxidation of the organic components in the sample to carbon dioxide. TOC is then computed from the difference (TOC= TC−IC). For samples containing high levels of inorganic carbon and lower levels of TOC, the Godec patent teaches an embodiment of the device where an IC removal module is used to remove the inorganic carbon and permit accurate TOC measurements.

Supplies of the acid and oxidizer may be pre-packaged and stored in the analyzer, eliminating the need for reagent preparation by the analyst. Deionized water is continuously produced in the analyzer using a mixed-bed ion exchange resin with a capacity for several years of operation. The maintenance required is replacement of the reagent containers several times a year, replacement of the UV lamp and replacement of the pump tubing. The ease of use, low maintenance requirements and dependable performance have made this device the TOC analyzer of choice for monitoring water purification systems in semiconductor manufacturing, the pharmaceutical industry and both conventional and nuclear power plants.

Some industries routinely use deionized water for various manufacturing and processing steps. In such industries, the accurate measurement of extremely low levels of TOC is often highly desirable. When the sample stream is known to be deionized water, the TOC detector described in the Godec patent contains several elements that are unnecessary and that make it less desirable for use in continuous rather than batch analysis of TOC. For example, the Godec device requires the use of chemical reagents to acidify the sample stream and to assist in the oxidation process. One of several important aspects of the present invention is the recognition that TOC analysis of deionized water samples does not require all the processing and pretreatment steps of TOC devices found in the prior art.

SUMMARY OF THE INVENTION

The present invention is directed to a method and apparatus for the detection and quantification of total organic carbon (TOC) in aqueous samples. In the preferred modes of the invention, the aqueous sample consists of deionized water, and the TOC analysis is accomplished on a continuous basis.

In one embodiment of the present invention, the aqueous sample stream is split into a first stream and a second stream. The first stream is directed into a first conductivity and temperature cell for a measurement of conductivity and temperature. The level of inorganic carbon, in the form of carbon dioxide, is calculated solely from the measurements in this first conductivity and temperature cell. Pure water has a pH of 7.0 (the concentration of $H^+$ and $OH^-$ species each being $1 \times 10^{-7} M$) and at any given temperature the conductivity is well known. Thus, any conductivity in excess of the known conductivity of pure water is deemed to be due to dissolved carbon dioxide.

All conductivity of the sample stream in excess of that attributable to pure water may be assumed to be derived from the ionizing effect of dissolved carbon dioxide ($CO_2 + H_2O \rightarrow H^+ + HCO_3^-$) because it is known that the sample stream is comprised of deionized water. In this context, "deionized water" means water that has been deionized according to procedures familiar to those skilled in the art, and that has no substantial ion concentration other than associated with pure water.

The sample in the first stream then passes into an oxidation module. In the oxidation module, organic compounds in the sample stream are converted to carbon dioxide. The oxidation module preferably utilizes direct U.V. oxidation, but may also or in addition use short wavelength U.V. radiation, semiconductor catalyzed U.V. oxidation using short wavelength U.V. radiation, electrochemically generated oxygen, or U.V. oxidation in the presence of oxygen and/or other non-ionic oxidizing agents. In the preferred embodiments of the invention, the U.V. radiation source is a narrow band excimer source or mercury vapor lamp. Oxidizing agents, if employed, may be generated in-situ by the electrolysis of water.

The ability of the oxidation module to oxidize organic species in the sample stream may be non-constant over time. For example, the oxidation module may operate in cycles in which the "oxidation potential" as defined herein changes gradually from a smaller to a larger value over an oxidation potential period such as three or four minutes. By gradually increasing, or "ramping," the oxidation potential over a timed cycle, it is possible to assure that the optimum oxidation is achieved at some point in the cycle. One method for varying the oxidation potential of the oxygen module is varying the duration of exposure of the sample stream to the U.V. radiation reactor. A slower flow rate will result in a longer exposure time and, therefore, a greater oxidation potential.

The carbon dioxide in the sample stream exiting the oxidation module is sensitively and selectively measured using a gas permeable membrane carbon dioxide sensor. The first sample stream that passes through the oxidation module is then introduced into the carbon dioxide separation module. The carbon dioxide separation module is comprised of a carbon dioxide selective gas permeable membrane that has a chamber on each side for receiving aqueous streams of solution. The oxidation module is in fluid communication with the first side of the carbon dioxide separation module.

The Godec patent described above teaches the use of a carbon dioxide sensor comprising a carbon dioxide selective gas permeable membrane which separates the sample stream from a source of deionized water. In the Godec patent, the deionized water is either continuously generated by passing water through a mixed bed ion exchange resin, or supplied from a source external to the apparatus. The carbon dioxide dissolved in the sample stream diffuses through the membrane and enters the deionized water. The carbon dioxide—dissolved in the water—causes an increase in the conductivity of the aqueous solution. The deionized water with dissolved carbon dioxide then flows into a conductivity cell in order to measure the increase in the concentration of ionic species. The conductivity (or, in the case of a system in which the oxidation potential is varied, the peak conductivity over an oxidation potential period) that is measured in the deionized water with dissolved carbon dioxide can be directly related to the concentration of carbon dioxide in the sample stream and hence the level of total carbon originally present in the sample stream.

In the present invention, the deionized water stream that is on the second side of the carbon dioxide separation module is the second stream split from the aqueous sample stream. It is possible to use this as the deionized water source since it is known that the sample stream is deionized water. Thus the second stream is used to accept the carbon dioxide that permeates through the gas permeable membrane.

In this preferred embodiment, a second conductivity and temperature measurement cell is downstream from the gas permeable membrane and is in fluid communication with the second side of the carbon dioxide separation module. This second conductivity and temperature measurement cell measures the concentration of carbon dioxide found in the second stream and hence the total carbon concentration in the sample stream. Both streams may then be discarded.

It can be appreciated that, although the device makes direct measurements of only inorganic carbon and total carbon, these two measurements can be used to determine total organic carbon as well. The determination of total organic carbon is accomplished by subtracting the measured inorganic carbon from the measured total carbon.

The present invention represents a dramatic improvement over the TOC detectors of the prior art for the measurement of TOC in deionized water sample streams. The method of measuring TOC is useful even when the deionized water sample stream contains some inorganic carbon in the form of carbon dioxide. The first conductivity and temperature measurement cell establishes a baseline for the conductivity of the sample stream. Conductivity in the first cell is attributable to the conductivity of pure water plus the conductivity of carbon dioxide, if any, contained in the sample stream being analyzed. The second conductivity and temperature measurement cell measures the conductivity of the second stream. The second stream contains a concentration of carbon dioxide that represents the equilibrium established in the carbon dioxide separator across the gas permeable membrane between the first and second streams. The difference between the conductivity measured in the two cells can be directly correlated to the amount of carbon dioxide formed by oxidation of the organic components in the sample stream within the oxidation module. The ability to correctly measure TOC in deionized water that also contains carbon dioxide allows for the easy preparation of organic carbon containing standards in normal laboratory environments, and does not require that the standards be isolated from the atmosphere.

The dimensions of the conduits and other flow-containing components are deliberately left quite small in the preferred embodiment. These small dimensions accommodate only a small volume and layer thickness of sample, thereby facilitating rapid sample turnover and short diffusion times. This results in rapid responsiveness of the device to changing sample concentrations. Rapid response is necessary for practical application in many industries. The small sample volumes are allowed even in water with very low carbon concentrations, because the device measures concentration directly (as it relates to conductivity) rather than being dependent on mass measurements which require substantial sample volumes when dealing with low concentrations.

In one alternate embodiment of the present invention, means are provided for introducing acid into the first stream after it exits the oxidation module and before it enters the carbon dioxide separator module. In another embodiment of the invention, a third conductivity and temperature measurement cell is located in the path of the first stream between the oxidation module and the carbon dioxide separation module. The conductance content of this cell may be used to quantitate the concentration of heteroorganic compounds in the sample stream. In an additional alternative embodiment for use of the device of the present invention for evaluating water samples that are not deionized, means are provided for deionizing the second sample stream before it enters the carbon dioxide separator module. In a further embodiment, a third conductivity and temperature measurement cell is located between the oxidation reactor and the carbon dioxide gas transfer module with acid addition after the third conductivity and temperature measurement cell.

DETAILED DESCRIPTION OF THE PREFERRED EMBODIMENT

The measurement of the total organic carbon of aqueous samples has become a standard technique for determining the quality of potable water, industrial process water and industrial and municipal waste waters. It also has become a standard technique for determining the purity of deionized water used in the manufacture and processing of electronic components and fine chemicals and pharmaceuticals.

The determination of the organic carbon content of water samples is most commonly achieved by oxidation of the carbon based constituents to carbon dioxide using chemical oxidizing agents, U.V. radiation, electrolysis, high temperature combustion, or a combination of these methods and the subsequent detection of the carbon dioxide using IR spectroscopy or by conductometric or potentiometric techniques. The present invention is an improved process and apparatus for determining concentration levels of total organic and inorganic carbon compounds in aqueous samples. The TOC detector of the present invention is particularly well suited for the continuous analysis of deionized water samples.

Figure 1:
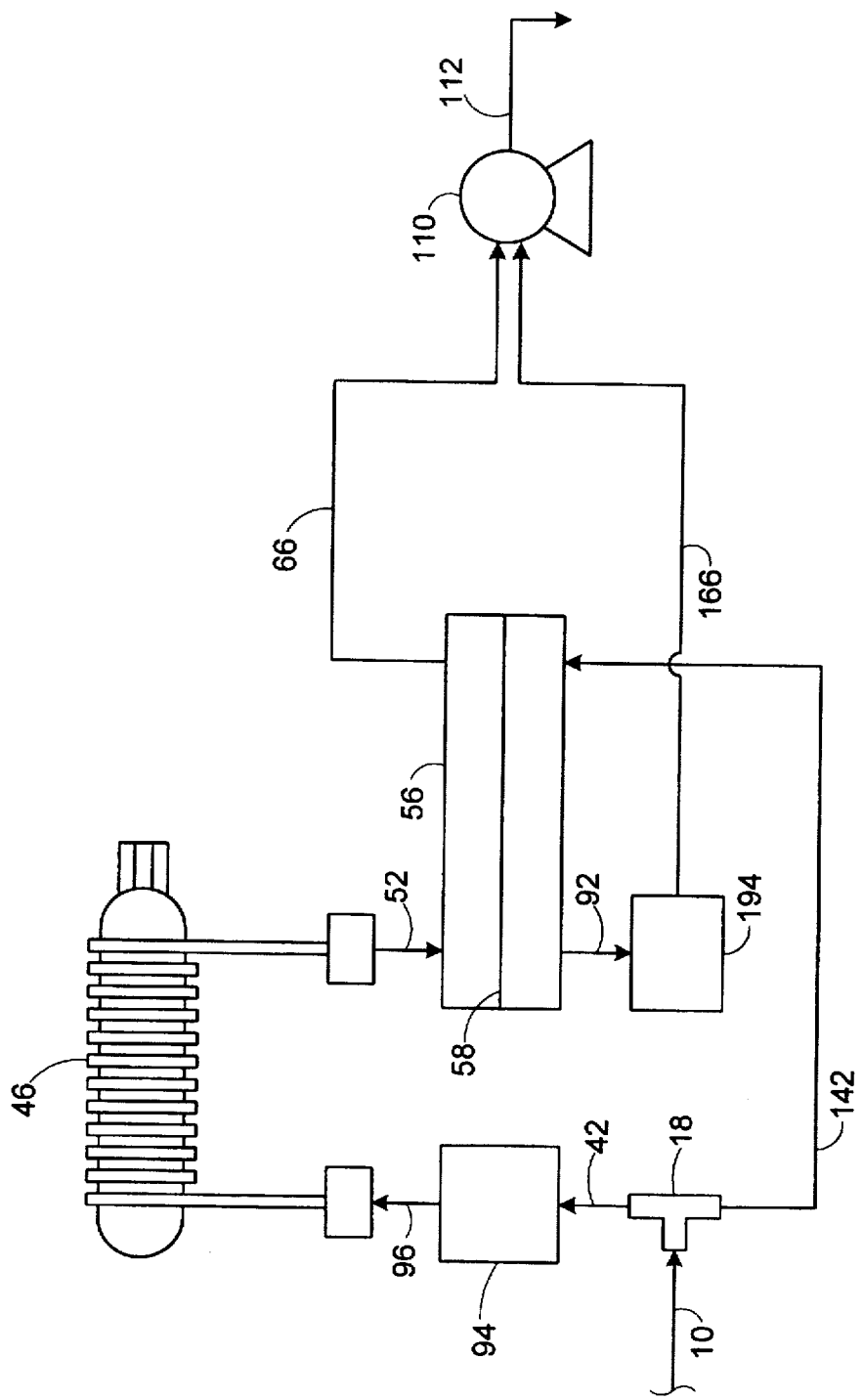
FIG. 1 is a block diagram depicting an embodiment of the present invention for the measurement of carbon concentrations in accordance with the present invention.

A block diagram of a preferred embodiment of the present invention is shown in FIG. 1. An aqueous sample inlet opening 10 is in communication with a tee fitting 18 which splits the sample into two streams, a first stream which flows through conduit 42 and second stream which flows through conduit 142. The conduit 42 leads to a first temperature and conductivity cell 94. The first temperature and conductivity cell 94, as well as the second temperature and conductivity cell 194 described below, in this preferred embodiment have a very small liquid volume on the order of less than 500 µL, more preferably 10 µL or less. This aids in very rapid response time for changing sample conditions. The design and manufacture of temperature and conductivity cells appropriate for use in the present invention are known to those skilled in the art.

The outlet of the first temperature and conductivity cell 94 leads to a U.V. oxidation reactor 46 through conduit 96. Several U.V. oxidation reactors are described in detail in U.S. Pat. No. 5,132,094 by Godec, the contents of which are hereby incorporated by reference. In the preferred embodiment of the oxidation reactor of the present invention the aqueous sample inlet of the U.V. oxidation module 46 is in communication with a coiled fused silica tube with an internal diameter of approximately 1 mm. The radius of the coil is such that a U.V. radiation source can be positioned in the annular region of the fused silica coiled tube. A suitable power supply and electrical connections (not shown) are used for the operation of the U.V. radiation source, which may consist of any known device which emits U.V. radiation, such as an excimer lamp, a gas discharge tube or mercury vapor discharge tube. An excimer lamp emitting light concentrated around 172 nm or other desired frequencies may be particularly useful. The design of the U.V. oxidation module has been demonstrated to provide high efficiency conversion of organic compounds to form carbon dioxide from aqueous samples.

The U.V. oxidation module outlet conduit 52 is in communication with the aqueous sample inlet of a carbon dioxide sensor which includes a carbon dioxide separator module or gas transfer module 56. The gas transfer module 56 includes a selective carbon dioxide gas permeable membrane 58 positioned such that the flowing aqueous sample of the first stream passes on the first side of the gas permeable membrane 58. The second side of the membrane 58 is in fluid communication with the second stream and passes deionized water or deionized water with dissolved carbon dioxide. It is important that the volume of the reservoir on each side of the membrane 58, and the total volume of the water contained within the gas transfer module 56, be kept quite small, in order to facilitate rapid response times. In a preferred embodiment, the deionized water on the second stream side of the membrane 58 is in a layer less than 0.06 inches thick and less than 1,000 µL in volume, more preferably a layer having a thickness of approximately 0.01 to 0.02 inch with a total volume of less than 150 µL.

Because this embodiment of the device is for use with samples that are known to be deionized water or deionized water with dissolved carbon dioxide, the source of deionized water for the second or deionized water side of the gas transfer module 56 is the unoxidized sample itself. Thus the second stream, which flows through the conduit 142, is used for this purpose. Conduit 142 is in communication with the second side of the gas transfer module 56 at the end opposite the end where the conduit 52 enters the first side of gas transfer module 56 to flow the first stream from the oxidation module 46. The counterflow produced by the first stream and second stream on either side of the gas permeable membrane 58 in the gas transfer module 56 results in the transfer of carbon dioxide from the first stream into the second stream to achieve equilibrium or near-equilibrium between the two streams. By utilizing the second stream of the sample itself for the deionized water needed in the gas transfer module 56, the device avoids the necessity for a separate deionized water source or a deionizing water resin bed.

The second stream flows from the second side of the gas transfer module 56 to a second temperature and conductivity cell 194 via conduit 92. The outlet of the second temperature and conductivity cell 194 flows through coduit 166 into pump 110 and is discarded through waste conduit 112. Similarly, the outlet of the first side of the gas transfer module 56 for the first stream flows through conduit 66 into pump 110 and is also discarded through waste conduit 112.

The temperature and conductivity cells 94 and 194 are connected to a suitable power supply (not shown) and their electrical outputs are connected to a control and signal electronics module (not shown). The control and electronic module is comprised of a computer or other electronic device which is capable of controlling the voltages and currents to all of the electrical components of the present invention, actuation of any necessary motors, valves and switches in a pre-determined timed sequence, processing of the electrical signal from the temperature and conductivity cells, and calculations of total organic carbon concentration, total carbon concentration and total inorganic carbon concentration from the output of the temperature and conductivity cells.

In the typical operation of the present invention as described in FIG. 1, the sampling pump 110—normally a peristaltic pump—withdraws an aqueous sample via the sample inlet conduit 10, at a desired flow rate. The flow rates through the first stream and second stream may be different. The different flow rates can be achieved with a single pump motor by utilizing a peristaltic pump accommodating both tubing of a first diameter for the first stream and tubing of a second diameter different from the first diameter for the second stream. The flow rates may also vary in the manner described below to ensure complete oxidation in the first stream. In the preferred embodiment, flow through the first stream is 340 µL/min and flow through the second stream is 40 µL/min.

The aqueous sample stream is split at fitting 18 into the first stream and the second stream. The first stream enters the first temperature and conductivity cell 94 where the temperature and conductivity of the sample are measured to determine the concentration of inorganic carbon. This measure provides a base-line conductivity measurement for the sample stream. Conductivity of the deionized sample stream not attributable to pure water is assumed to be attributable to the conductivity associated with carbon dioxide dissolved in the aqueous sample stream.

The first stream then leaves the first temperature and conductivity cell 94 and flows to the U.V. oxidation reactor 46 via conduit 96. Organic compounds are converted to carbon dioxide and other products in the U.V. oxidation reactor 46. In the preferred embodiment the U.V. source is a low pressure mercury vapor lamp emitting at about 184 and 254 nm. In an additional preferred embodiment, an excimer lamp with strong bands at 172 and 190 nm may be used. The effluent of the U.V. oxidation reactor 46 is directed via conduit 52 into the first side of the aqueous sample inlet of the first side of the gas transfer module 56, out through the aqueous sample outlet of the first side of the gas transfer module 56, and through the peristaltic sample pump 110 to a suitable waste container.

The second stream is directed via conduit 142 into the inlet of the second or deionized water side of the gas transfer module 56, where dissolved carbon dioxide permeates into the second stream from the first stream through the carbon dioxide permeable membrane 58. Equilibrium or near equilibrium with respect to carbon dioxide concentrations is established across the membrane, and it can be assumed that the concentration of carbon dioxide in both first and second streams reaches a constant steady state concentration and, given sufficient contact time, approaches equality as each stream exits its respective side of the gas transfer module 56. The second stream flows out through the outlet of the second side of the gas transfer module 56 and into the second temperature and conductivity cell 194, where the temperature and conductivity of the second stream are measured to determine the concentration of total carbon. The second stream then flows through the peristaltic sample pump 110 to the waste container. The measurements at the temperature and conductivity sensors 94 and 194 can take place virtually continuously or at periodic intervals by appropriate switching of the electronic measurement equipment.

It can be appreciated that the device and method of the present invention can be used to make one or more of several determinations. Total carbon concentration of the sample stream can be determined by the second temperature and conductivity cell 194. The inorganic carbon concentration of the sample stream can be determined by the first temperature and conductivity cell 94, assuming that the inorganic carbon in the sample is in the form of carbon dioxide dissolved into deionized water. Finally, the total organic carbon concentration of the sample stream can be determined by subtracting the inorganic carbon concentration from the total carbon concentration. Therefore, the device of the present invention can be used to accurately measure total organic carbon even if the sample contains dissolved carbon dioxide. Ionic contamination due to the presence of carbon dioxide will raise the conductivity measured in the first temperature and conductivity cell, but it will also raise the conductivity measured in the second temperature and conductivity cell. When the organic carbon concentration is determined by subtracting the carbon dioxide concentration calculated from the measurement in the first temperature and conductivity cell from the carbon dioxide concentration calculated from the measurement in the second temperature and conductivity cell, the increase in carbon dioxide concentration due to the presence of dissolved carbon dioxide in the sample stream will cancel out to give a true determination of total organic carbon concentration.

It can also be appreciated that there is some flexibility in the arrangement of the various components. For example, the first temperature and conductivity cell 94 could be in the second stream 142 rather than in the first stream (although such an arrangement could introduce ionic contamination from the first temperature and conductivity cell into the second stream where it could distort the measurements in the second temperature and conductivity cell).

An important advantage to the present invention is that the oxidation potential applied to the sample can be varied over a period of time in order to ensure that complete oxidation takes place in the first stream. The term "oxidation potential" is used herein to mean the potential for oxidation of a compound due to an oxidizing source such as, in the preferred embodiment, the U.V. oxidation reactor. The period of time over which the oxidation potential is varied is referred to herein as the "oxidation potential period." The benefit of varying the oxidation potential to the sample is that one can thereby ensure that complete oxidation is obtained in the first stream for a wide range of organic carbon concentrations. In the prior art, a single oxidation potential is generally used. When using a single fixed oxidation potential it is often impossible to achieve complete oxidation for hard to oxidize carbon compounds. To the extent that oxidation of any organic components of the sample stream is incomplete, the measure of TOC concentration will be less than actual.

The oxidation potential can be varied over the oxidation potential period in several ways. One method is to vary the intensity of the U.V. radiation that irradiates the first stream in the U.V. oxidation reactor. Another method is to vary the duration of U.V. radiation exposure by lengthening or shortening the amount of tubing exposed to the U.V. source that the first sample stream will pass through, or varying the flow rate of the first stream through the U.V. oxidation module. This latter method is accomplished in a straightforward manner by simply varying the speed of the sample pump. The variation in oxidation potential can be in any desired pattern. The simplest patterns are to vary linearly, depending on the expected carbon concentration variations, from a minimum to a maximum value or from a maximum level of U.V. exposure to a minimum.

Figure 2:
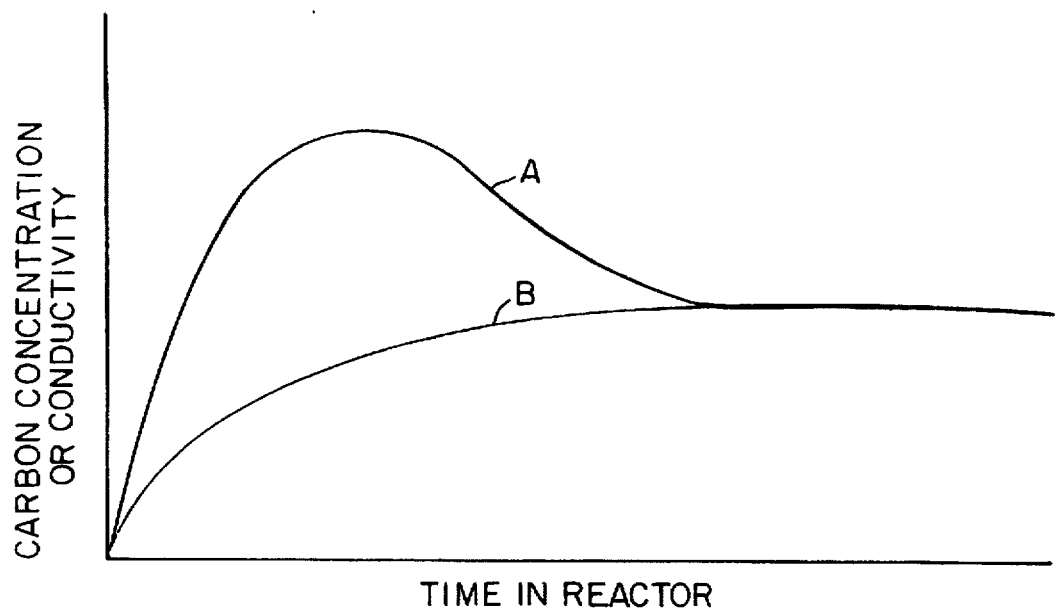
FIG. 2 is a graph of measured conductivity versus time of exposure to an oxidation reactor for several samples using prior art devices and devices of the present invention.

The graph of FIG. 2 illustrates the measurement problems that can be encountered if incomplete oxidation occurs in certain kinds of samples, particularly if the detector does not utilize specific membrane transfer of carbon dioxide in the sensing portion as taught in the present invention. The vertical axis is the measured conductivity, and the horizontal axis is the duration of time during which the sample is subjected to an oxidation potential. Each curve represents the measured conductivity in a temperature and conductivity cell downstream from an oxidation reactor, which relates to the determined organic carbon concentration. Curve A depicts for example, the result of oxidation of an acetone-containing sample in a non-membrane or non-selective membrane sensing system. (For example, the device taught in U.S. Pat. Nos. 4,660,860 and 4,626,413 of Blades, et al., or the embodiment of this invention shown in FIG. 3, or the embodiment of this invention depicted in FIG. 1 where a non-selective gas permeable membrane is used.) The peak in curve A is due to the production of intermediate oxidation products such as ionic organic acids generated from oxidation of the acetone. These intermediates have high dissociation constants which result in high measured conductivity. As the extent of oxidation increases, toward the right on the horizontal axis, the intermediate ionic organic acids gradually are oxidized to carbon dioxide so that the measured conductivity decreases and eventually becomes constant. This constant represents complete oxidation, where there are substantially no remaining ionic organic acids to produce an erroneously high conductivity measurement, and at the same time all organic carbon specimens have been fully oxidized to carbon dioxide. Thus the true organic carbon concentration can be derived from this conductivity measurement. Curve A is typical of samples that contain any organic compounds that have partial oxidation products that are ionic.

It can be appreciated from the graph of FIG. 2 that incomplete oxidation in a non-selective membrane or non-membrane type system can lead to grossly erroneous measurements. The erroneous measurement can be much too high if the oxidation reaction ends when there are ionic organic acids formed as intermediates, as represented by the peak of curve A of FIG. 2. Moreover, one cannot accurately predict the shape of the curve without prior knowledge about the nature of the sample. For example, one cannot mathematically derive the constant value which represents a true measurement due to complete oxidation with only the data of a few points on the positively sloping portion of the curve. This is because, without knowledge of the nature of the sample, such as can be obtained by subjecting the sample to complete oxidation to produce the entire curve of conductivity as a function of oxidation time, there is no way to know if the data will in fact produce the shape of the top curve or will instead assume some other shape such as the shape of curve B. Curve B represents a typical conductivity analysis for an aqueous sample containing one or more organic compounds that do not form intermediate ionic oxidation products (methanol). For these types of samples conductivity measured using the membrane detector of the present invention will give the same result as methods measuring carbon dioxide via other methods. Curve B also represents the measurement that is obtained in the device of the present invention where the sample is the same (acetone) as shown in curve A.

Stated another way, in analyzing curve A there is no way to know without knowledge of the sample whether the data represent conductivity due to the formation of intermediates. If one were to simply assume that the data represent conductivity due to the formation of intermediates, and therefore one were to extrapolate the top curve from points generated on the initial positively sloping portion, the resulting determination of organic carbon will be erroneously low if that assumption is wrong. Conversely, if one were to simply assume that the data do not represent conductivity due to the formation if the intermediates and instead represent solely conductivity due to organic carbon oxidized into carbon dioxide, and therefore one were to extrapolate a curve such as curve B from points generated on the positively sloping portion, the resulting determination of organic carbon will be erroneously high if that assumption is wrong.

Curve B of FIG. 2 shows the result of oxidation of the same acetone-containing sample as shown by the top curve of FIG. 2, but now using a selective membrane-based system as taught herein (in which the sample is oxidized to produce carbon dioxide, the carbon dioxide permeates through a selective carbon dioxide permeable membrane into deionized water, and the conductivity of the deionized water with dissolved carbon dioxide is measured in a conductivity cell). The conductivity of an acetone-containing sample as a function of oxidation time is grossly different between selective membranebased and non-membrane-based or non-selective membrane based carbon dioxide detectors. Ionic organic intermediates never reach the conductivity cell in the present invention. The result is that incomplete oxidation of an acetone-containing sample in the present system will not produce an erroneously high organic carbon determination. The measurement of conductivity as a function of oxidation time produces a smooth curve that gradually increases toward a plateau value from which the true organic carbon concentration can be determined, instead of producing a false peak depending on the unknown nature of the sample. The use of Gore-tex or microporous hydrophobic membranes as taught in the Carlson patent will not give the appropriate selectivity to carbon dioxide diffusion. (See, U.S. Pat. No. 5,132,094 of Godec).

The principles demonstrated in FIG. 2 have several important ramifications in the operation of the present apparatus. One is that it allows for a simple and certain process for determining whether complete oxidation has occurred. By adjusting the sample flow rate through the oxidation reactor, if the measured conductivity at two different flow rates is substantially the same, then it is possible to conclude that both conductivity points are on the plateau portion of the conductivity/time curve of FIG. 2. Therefore, there has been substantially complete oxidation in both measurements, and the conductivity produced by such oxidation can be used to determine accurately the true organic carbon concentration. When the nature and concentration of the contaminants in a sample will be generally the same, it is possible to establish the appropriate minimum flow rate required to obtain complete organic oxidation. Establishment of the minimum time period allows the user to increase throughput and more instantaneously monitor TOC levels in the sample stream.

In a non-membrane system or a non-selective membrane system, the fact that the measured conductivity at two different flow rates is substantially the same does not necessarily mean that the points are on the constant (complete oxidation) portion of the conductivity/time curve. Instead, in the case of, for example, an acetone-containing sample, the points could be on either side of the peak shown in curve A of FIG. 2. If the nature of the organic components in the sample is not known, there is no way to know whether the two points are straddling the peak of a curve A generating sample, or are on the plateau portion of curve A or curve B generating sample. In practice, this feature allows the system of the present invention to routinely make accurate organic carbon determinations with as little as two conductivity measurements. The process is simply to make a first conductivity measurement using a first sample flow rate, to make a second conductivity measurement using a second sample flow rate, and to compare the two conductivity measurements to determine whether the difference is within a pre-established threshold indicating that the points are sufficiently on the plateau portion of the conductivity/time curve that they reflect substantially complete oxidation of the sample. If they are, then the organic carbon concentration can be determined from either value. If the results deviate, then a third conductivity measurement is taken using a flow rate slower than either of the first two. The conductivity measurement using that third flow rate is compared with the conductivity measurement using the flow rate just faster than the third flow rate, in order to determine whether that difference is within the pre-established threshold. This process can be repeated until the reduction in flow rate does not result in a significant increase in conductivity.

Another important ramification of the feature demonstrated in FIG. 2 in the operation of the apparatus of the present invention is that it allows mathematical extrapolation of the conductivity of the completely oxidized sample, using a small number of data points generated by incomplete oxidation. Because the conductivity/time curve produced by the system is a smooth curve with positive slope throughout until it reaches the plateau representing complete oxidation (as shown in curve B of FIG. 2), it is relatively easy to fit an exponential or other suitable function to a few data points to produce an accurate prediction of the constant plateau value. This is much more difficult in a non-membrane based system (as represented by curve A of FIG. 2) because there is no way to know in advance the general shape of the conductivity/time curve.

The discussion above assumes that the oxidation potential is varied by varying the sample flow rate through the oxidation reactor to produce variations in the period of time during which the sample is subjected to the oxidizing effects of U.V. radiation. As explained previously, the same effect could be achieved by varying the oxidation potential in other ways, such as by varying the intensity of the U.V. radiation in a U.V. oxidation reactor. It is also possible to calculate a carbon dioxide concentration from the conductivity and temperature data and plot it in the same way as FIG. 2 and to evaluate for the completion of oxidation in the same way as is done with conductivity.

Figure 3:
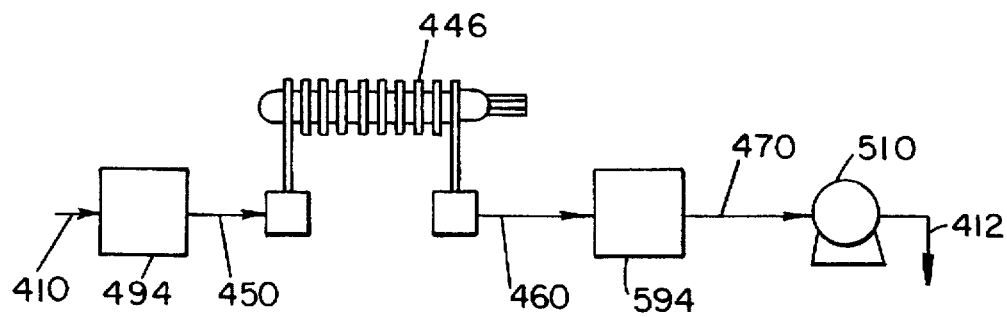
FIG. 3 is a block diagram depicting an alternate embodiment of the present invention.

As explained above, non-membrane based systems can suffer from erroneous carbon determination if the oxidation reaction is incomplete, due to the formation of ionic organic acids with high conductivity. This problem can be avoided, however, if such a system is operated in a manner that ensures complete oxidation. A block diagram of a simple such system is shown in FIG. 3. A sample inlet conduit 410 leads to a first temperature and conductivity cell 494 which measures the conductivity due to the inorganic carbon concentration in the sample. The outlet conduit 450 from the first temperature and conductivity cell 494 leads to a U.V. oxidation reactor 446 which fully oxidizes all organic carbon in the sample to produce dissolved carbon dioxide. In the preferred orientation of this embodiment of the present invention, a U.V. oxidation reactor is utilized as described above; however, any oxidation reactor capable of fully oxidizing the organic components of the sample could be used in this embodiment. The stream then flows to the second temperature and conductivity cell 594 through conduit 460. The second temperature and conductivity cell 594 measures the conductivity due to inorganic carbon plus the conductivity due to carbon dioxide produced by the oxidation of organic carbon in the U.V. oxidation reactor 446. The stream leaves the second temperature and conductivity cell 594 through conduit 470, passes through pump 510 and is discarded through waste line 412.

It can be appreciated that the system shown in FIG. 3 can be used to determine the concentration of inorganic carbon (assuming dissolved carbon dioxide is found in the deionized water) in the sample using the first temperature and conductivity cell 494, and can determine the concentration of total carbon in the sample using the second temperature and conductivity cell 594, subject to some important limitations. The first limitation is that the sample must be substantially deionized water, or deionized water with carbon dioxide dissolved in it. The presence of other ions in the sample stream will be conductive and incorrectly interpreted as carbon dioxide.

The second limitation is that ionic contamination from the reactor or from products of the oxidation other than carbon dioxide (such as $Cl^-$ or $SO_4^=$) will produce erroneously high carbon analysis because the non-membrane system has no ability to distinguish between conductivity resulting from carbon concentrations and conductivity resulting from other ionic species. The third limitation is that the measurements will be inaccurate if the reaction is not allowed to proceed to obtain substantially complete oxidation in order to ensure that substantially all organic carbon and intermediates have been oxidized to ionic species that are measurable in an accurate way by the second temperature and conductivity cell 594. This third limitation can be addressed by varying the oxidation potential over an oxidation potential period and taking several conductivity measurements during that period in the second temperature and conductivity cell 594. The conductivity should vary over the oxidation potential period due to the varying production of carbon dioxide by oxidation of organic carbon, until the oxidation is substantially complete. At that point, there is no additional organic carbon to be oxidized, and so increasing the oxidation potential will have no appreciable effect on the conductivity measurements in the second temperature and conductivity cell 594.

In operation, the oxidation potential is preferably varied by simply varying the speed of the pump 510 to vary the sample flow rate. A lower pump speed will reduce the flow rate and thereby expose the sample to the U.V. oxidation reactor for a longer duration of time, while a higher pump speed will increase the flow rate and thereby expose the sample to the U.V. oxidation reactor for a shorter duration of time. The oxidation potential is greater, and therefore, the oxidation of the sample is more likely to be complete, at the lower pump speed. The oxidation potential is less, and therefore the oxidation potential is more likely to be incomplete, at the higher pump speeds.

By varying the pump speed to produce varying oxidation potential over an oxidation potential period, one can ensure that substantially complete oxidation occurs at some point in the period. Moreover, it is relatively easy to ascertain that point by comparing the conductivity from one pump speed—or sample flow rate—to the next. For example, conductivity measurements that are grossly different from one flow rate to an incrementally different flow rate are indicative of incomplete oxidation; the two conductivity points do not lie on the plateau portion of the conductivity/time curve that results from substantially complete oxidation of the sample. On the other hand, conductivity measurements that are substantially the same from one flow rate to an incrementally different flow rate are generally indicative of substantially complete oxidation; the two conductivity points lie on the plateau portion of the conductivity/time curve that results from substantially complete oxidation. A peak of conductance can be differentiated from the plateau by using flow rates that will insure that both sides of the peak will be detected.

The variation in flow rate, thus oxidation potential, can be combined with the comparison of conductivity between adjacent data points in the manner previously described above in connection with other embodiments.

This process can be implemented in several ways. An effective approach is to start the flow rate at a high value to produce a low oxidation potential, and then gradually decrease the flow rate to produce gradually increasing oxidation potentials over the duration of the oxidation potential period. This will result in a series of data points from left to right on the conductivity/time curve of FIG. 2, so that the entire curve will be apparent. The plateau portion of the curve at which oxidation is substantially complete will thus be readily apparent, to allow derivation of the true carbon content of the sample. Because the embodiment of this invention depicted in FIG. 3 does not utilize the membrane based carbon dioxide measurement, the conductivity/time curve may look like either curve A or curve B, depending on the nature of the sample. However, the shape of the curve is not important if complete oxidation is obtained.

Having the data to generate the entire conductivity/time curve through the plateau portion will also provide some information about the nature of the sample; a curve in the shape of curve A of FIG. 2 will suggest that the sample contains organic materials such as acetone that result in high-conductivity intermediates on the way to complete oxidation. Further, operating the system in a manner that gradually increases the oxidation potential over the oxidation potential period allows one to cut short the oxidation potential period when the increase in conductivity between adjacent measurements is low, indicating that the data points are onto the plateau portion of the conductivity/time curve which is indicative of substantially complete oxidation. Thus, for example, an oxidation potential period of 300 seconds over which the pump rate gradually or incrementally increases oxidation potential, can be discontinued at 200 seconds if the data indicate that substantially complete oxidation has already occurred at that point. Conversely, an oxidation potential period of 300 seconds over which the pump rate decreases to produce an increasing oxidation potential, can be lengthened if the data indicate that substantially complete oxidation has not occurred even at the 300 second point.

It will be apparent that this comparison process must involve more than only two adjacent data points, and can involve a determination more sophisticated than simply comparing the measured conductivity between two adjacent measurements. For example, without limitation, the comparison could involve determining whether three or more conductivity measurements are within a given range of values, and could involve an analysis of the trend of conductivity. Further, there could be a predictive routine whereby several data points short of complete oxidation are fitted with an exponential or other appropriate mathematical function to predict the conductivity at substantially complete oxidation. It can be appreciated that the embodiment of FIG. 1 requires less time and data to determine if oxidation is complete than the embodiment of FIG. 3.

Figure 3A:
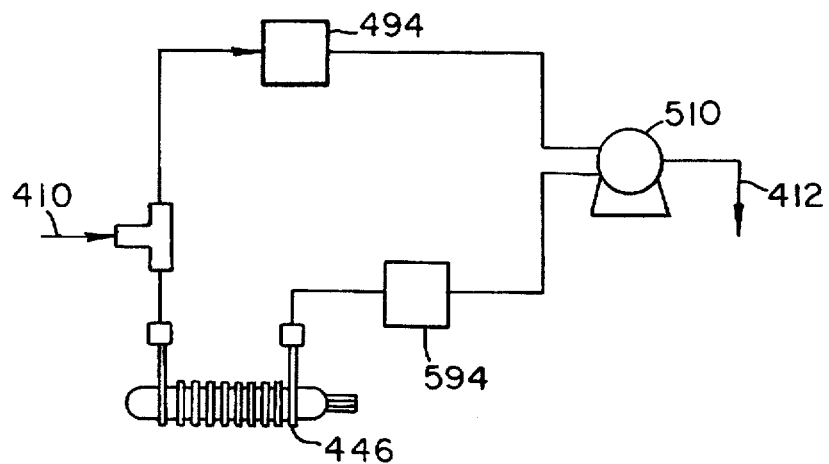
FIG. 3A is a block diagram depicting an alternate embodiment of the present invention.

In a variation of the embodiment of FIG. 3, the sample stream is split into first and second streams, and the first temperature and conductivity cell 494 is placed in the second stream, as shown in FIG. 3A. This embodiment has the advantage of allowing the determination of inorganic carbon by the first temperature and conductivity cell 494 to be made at the same time as the determination of total carbon by the second temperature and conductivity cell 594. By the use of appropriate tubing sizing or delay tubing or different flow rates through the tubing of the first and second stream, simultaneous measurements can be made. In addition, there is no danger that the first stream will become contaminated by the first temperature and conductivity cell 494 which would distort the measurements in the second temperature and conductivity cell 594.

Prior art TOC detectors that do not use selective carbon dioxide gas permeable membranes while relying on carbon dioxide conductivity measurements have an additional serious problem. Certain heteroorganic compound impurities (compounds containing a halogen, N, S or P) in the sample stream can generate highly ionic species even after complete oxidation has occurred. The presence of these non-carbon based species leads to the measurement of conductance not attributable to carbon dioxide. The most common example of heteroorganic compounds that present this phenomena are halogenated hydrocarbons. Halogenated organic species are not ionic and can often be found in deionized water sources. However, upon oxidation halogenated organics will generate ion $X^-$ species ($F^-$, $Cl^-$, $Br^-$), that will significantly increase the conductance of the oxidized water stream. When referring to halogenated compounds throughout this application, it should be appreciated that other organic compounds containing hetero atoms can give rise to similar effects. For example, neutral nitrogen, sulfur or phosphorus containing organic compounds may also give rise to fully oxidized ionic species is ($NO_3^-$, $SO_3^{-2}$, $PO_3^{-3}$) that will artificially increase the carbon dioxide conductance measurements obtained in non-membrane based TOC detectors. One test of the present invention was for the measurement of chloroform in deionized water at concentrations varying from 1 to 250 ppb. As described above, certain prior art TOC detectors provide highly inaccurate measurements for halogen containing organic compounds due to the generation of ionic, fully oxidized species that will increase the conductivity of the oxidized sample stream. The results from this test demonstrated that the analysis obtained using the apparatus described in U.S. Pat. No. 5,132,094 of Godec et al.—as well as the embodiments of this invention shown in FIGS. 5 and 6—are not susceptible to error due to the presence of a halogen containing organic in the sample. The embodiment of the present invention depicted in FIG. 1, shows some deviation from absolute, but is relatively accurate. However, the embodiment shown in FIG. 3 and the device described in U.S. Pat. No. 4,626,413 give large errors. The error found in the TOC analysis for the halogenated organic when using the present invention FIG. 1 embodiment arises from the pH change that occurs in the first stream following oxidation. The pH effects the carbon dioxide equilibrium, and therefore the conductance in the second stream, even though only carbon dioxide is transported across the selective membrane. The ability to more accurately measure TOC concentrations when halogenated organics are found in the sample stream represents a dramatic improvement over the device disclosed in the Blades and Godec patent, which is the most commonly commercially utilized TOC analyzer for continuously monitoring deionized water.

Figure 7:
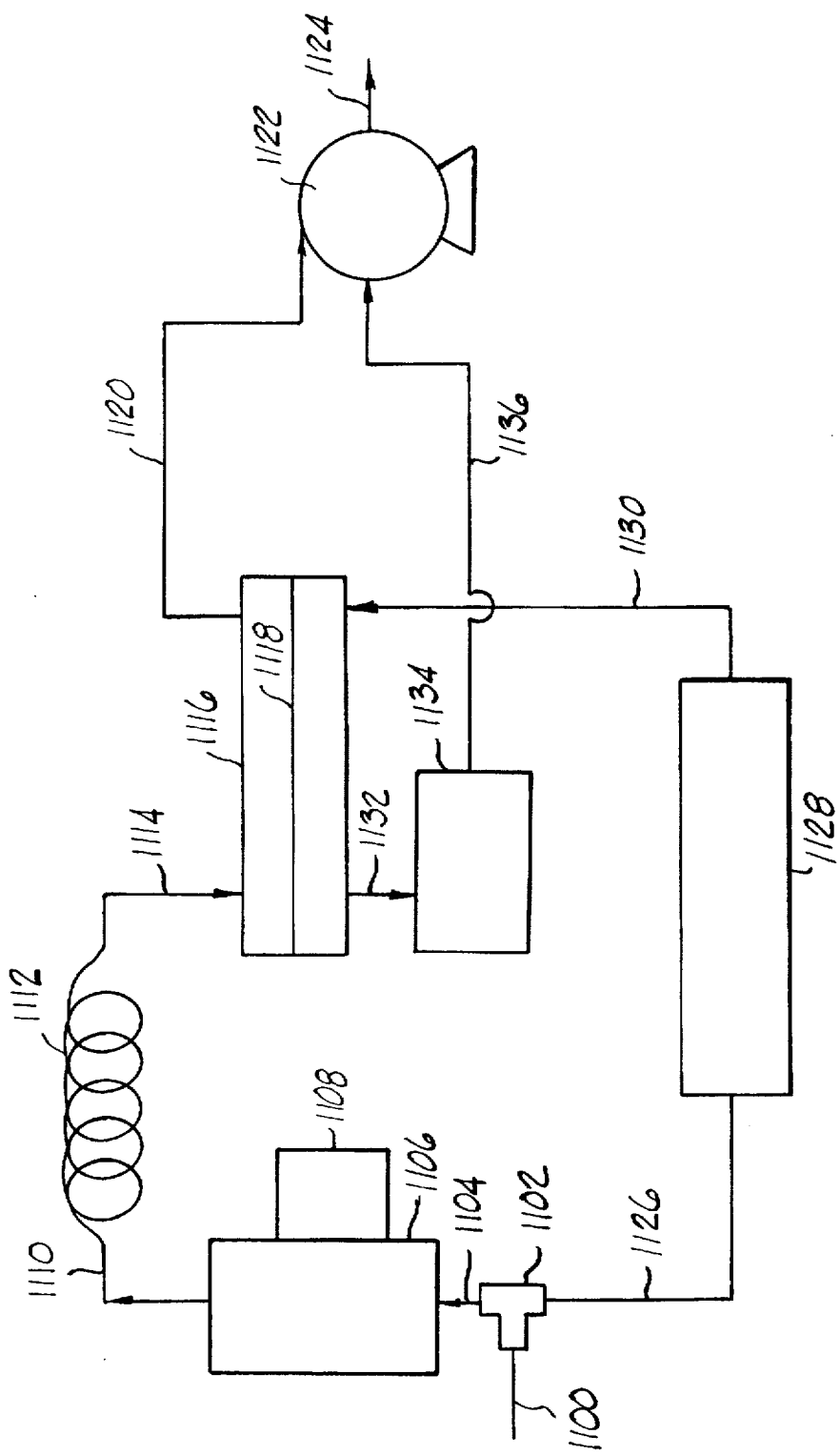
FIG. 7 is a block diagram depicting an alternate embodiment of the present invention wherein a device as in FIG. 1 includes a water deionization module in the second sample stream.
Figure 9:
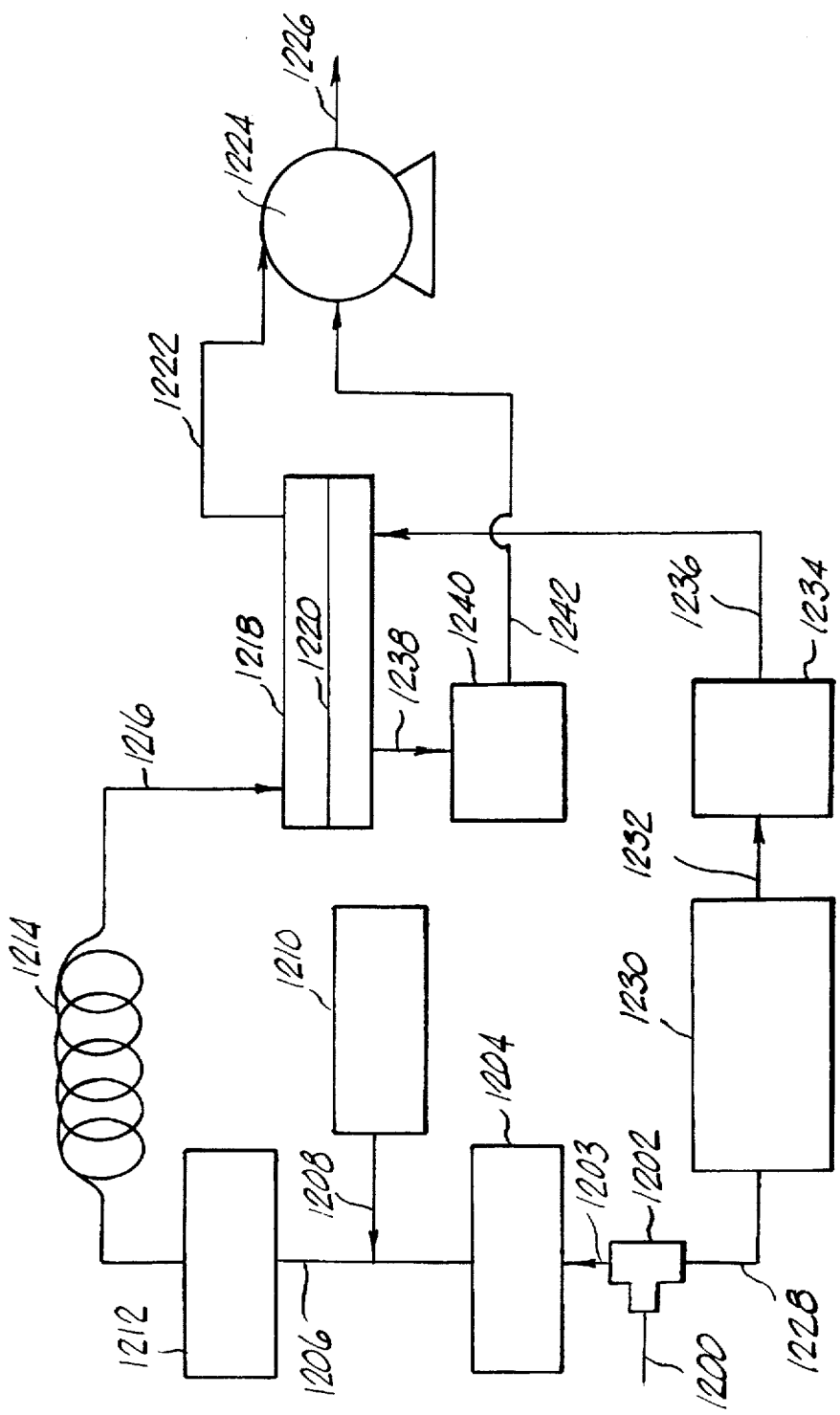
FIG. 9 is a block diagram depicting an alternate embodiment of the present invention including a water deionization module, an acidification module and an inorganic carbon removal module.

In another test of the present invention organic compound in the sample was acetic acid. In this case, the apparatus described in U.S. Pat. No. 5,132,094 and embodiments of the present invention depicted in FIGS. 7 and 9 show no predictable deviation from accuracy. Due to the acidity of the organic component in the sample stream, the FIG. 1 embodiment demonstrates some acceptable error, while the FIG. 3 embodiment and the device of U.S. Pat. No. 4,626,413 show significant errors.

Finally, in a third test of the present invention (and measured for the FIG. 1 embodiment), the sample contained an organic component and sodium chloride. The embodiments shown in FIGS. 7 and 9 herein, and the detector described in U.S. Pat. No. 5,132,094 should not be affected by the presence of sodium chloride. The predicted error for the FIG. 1 and FIG. 3 embodiment and for the detector described in U.S. Pat. No. 4,626,413 are identical.

Figure 4:
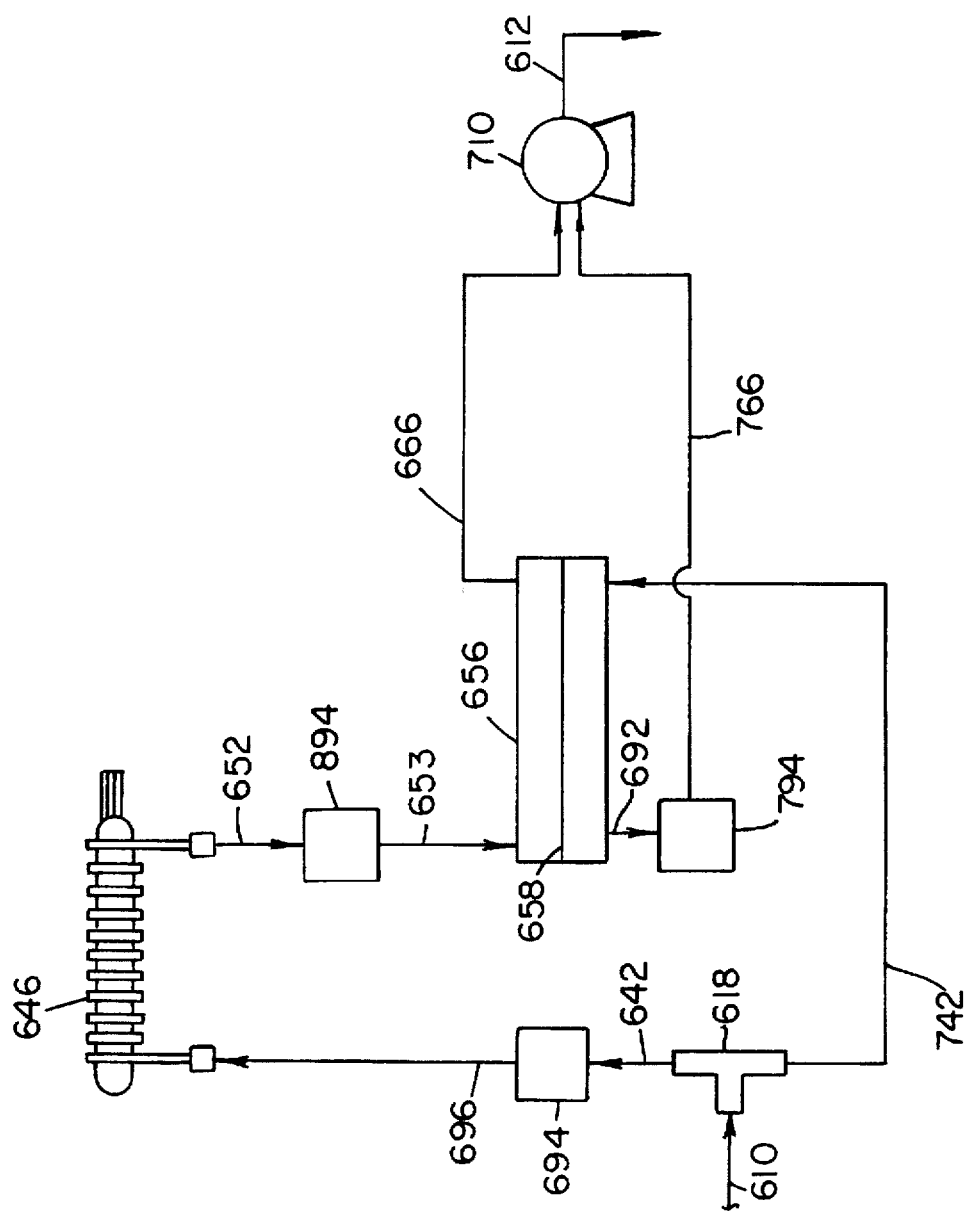
FIG. 4 is a block diagram depicting an alternate embodiment of the present invention.

Because of the artificial readings that are generated by heteroorganic compounds, an additional embodiment of the apparatus of the present invention is shown in FIG. 4, in which a third temperature and conductivity cell is employed so that a determination of the concentration of heteroorganic hydrocarbons can be made. The overall configuration of the device of FIG. 4 is similar to that of the device of FIG. 1, except for the additional temperature and conductivity cell. The sample enters the apparatus through a sample inlet 610 which leads to a fitting 618 which divides the sample into a first stream which flows through a first stream conduit 642 and a second stream which flows through a second stream conduit 742. Conduit 642 leads to a first temperature and conductivity cell 694 which measures the inorganic carbon concentration. The first stream then leaves the first temperature and conductivity cell 694 via conduit 696 and flows to a U.V. oxidation reactor 646 to convert organic carbon into carbon dioxide. The effluent of the U.V. oxidation reactor 646 is directed via conduit 652 into the third temperature and conductivity cell 894 where a "total carbon plus hetero ion concentration" is measured. The first stream then flows through conduit 653 into the first side of gas transfer module 656 for transfer of dissolved carbon dioxide across the carbon dioxide permeable membrane 658 into the second stream. The first stream then leaves the first side of the gas transfer module 656 via conduit 666, and flows through pump 710 and out waste line 612.

The second stream after being split from the first stream at conduit 618 is directed via conduit 742 into the inlet of the second or deionized water side of the gas transfer module 656, where dissolved carbon dioxide permeates into the second stream from the first stream through the carbon dioxide permeable membrane 658. The second stream, now with dissolved carbon dioxide, flows out through the outlet of the gas second side of the transfer module 656 and into the second temperature and conductivity cell 794 via conduit 692. The second temperature and conductivity cell 794 is used for a measurement of dissolved carbon dioxide concentration which can be related to the concentration of total carbon, not including ionic halogen species (or other hetero ion species) which cannot permeate through the carbon dioxide permeable membrane 658 of the gas transfer module 656. The second stream then flows through conduit 766 to the pump 710 and out the waste line 612.

The embodiment of FIG. 4 thus makes several determinations in a substantially deionized water sample. The first temperature and conductivity cell 694 can be used to determine inorganic carbon concentration. The second temperature and conductivity cell 794 operates identically to the similarly placed cell in the embodiment of FIG. 1 and can be used to determine total carbon concentration (the conductance arises from the inorganic carbon concentration, plus the organic carbon concentration related to the carbon dioxide produced by oxidation of organic carbon) but not including interference that increases the conductance arising from fully oxidized ionic species generated by the oxidation of heteroorganic compounds which are blocked by the gas permeable membrane 658. The third temperature and conductivity cell 894 generates a total carbon concentration that is artificially high due to the increase in conductivity caused by the inorganic halogen ionic species. Thus the system directly measures inorganic carbon concentration, total carbon (not including hetero hydrocarbon) concentration and total carbon (including hetero hydrocarbon) concentration. From these, the system can also be used to determine indirectly the halogenated hydrocarbon concentration by subtracting the determinations of total carbon (not including hetero hydrocarbon) from total carbon (including hetero hydrocarbon).

As the other embodiments described here, the device of FIG. 4 can be operated under varying oxidation potentials to ensure substantially complete oxidation in the U.V. oxidation reactor 646 and to allow for the use of mathematical fitting functions to predict the outcome of substantially complete oxidation even with only a limited number of data points from incomplete oxidation.

In a variation of the embodiment of the apparatus of the invention depicted in FIG. 4, it is possible to determine the total heteroorganic compound content of non-deionized water samples, such as drinking water. According to this variation (not shown), means are provided for removing from the first sample stream all inorganic carbon species, low molecular weight organic compounds (e.g., $CH_4$, $C_2H_6$) and ionic heteroorganic compounds (e.g., $ClCH_2COOH$) and trapping all organic species. These means would be followed by a water deionization module, and then means for adding the trapped organic species back into the first sample stream prior to oxidation. This variation would further include a water deionization module in the second sample stream. Utilization of this variation of the invention makes it possible to determine total heteroorganic carbon content of a non-deionized sample stream.

Figure 5:
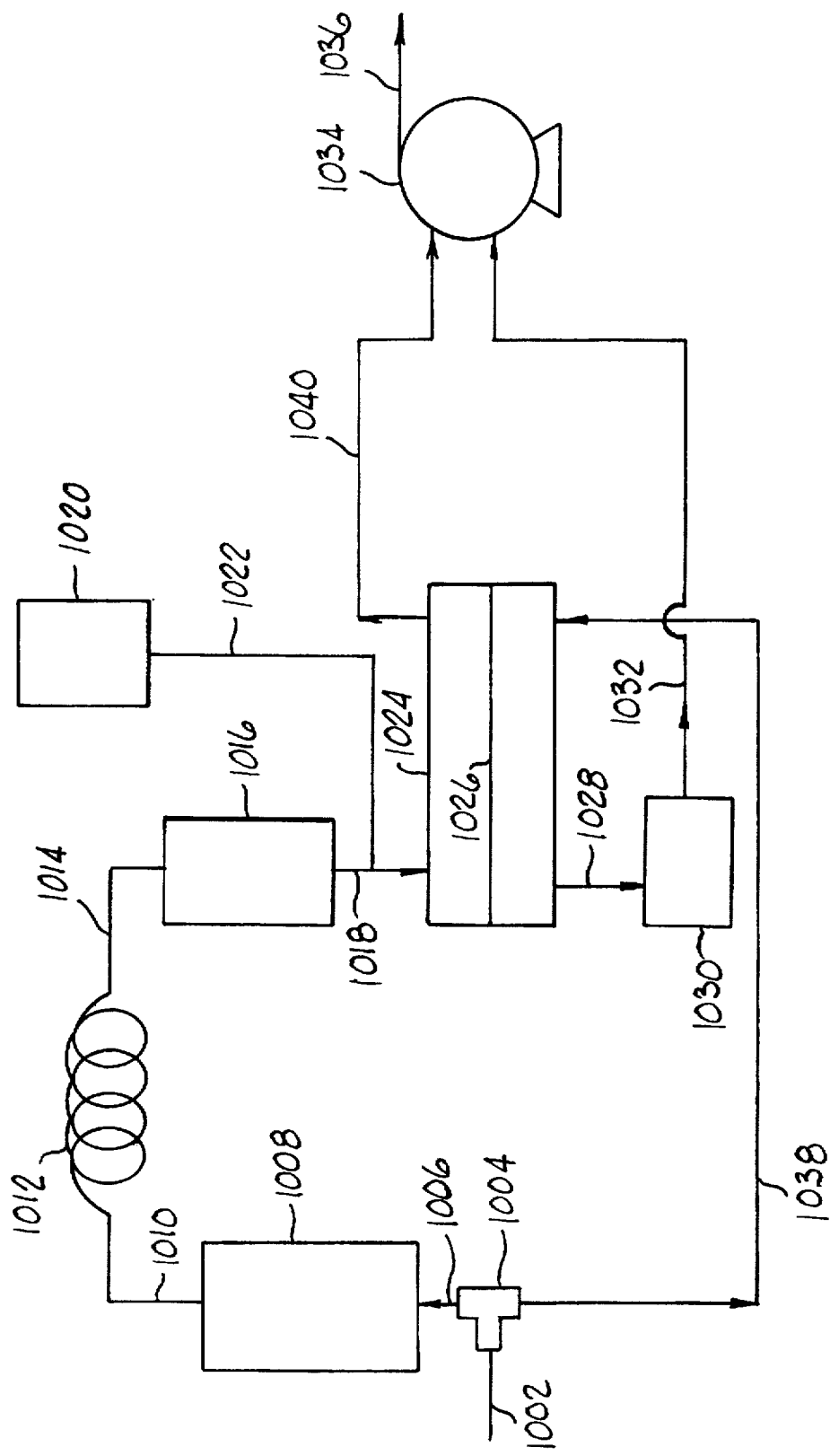
FIG. 5 is a block diagram depicting an alternate embodiment of the present invention wherein the sample exiting the oxidation reactor passes into a conductivity and temperature measurement cell and is acidified before being introduced into the gas transfer module.
Figure 6:
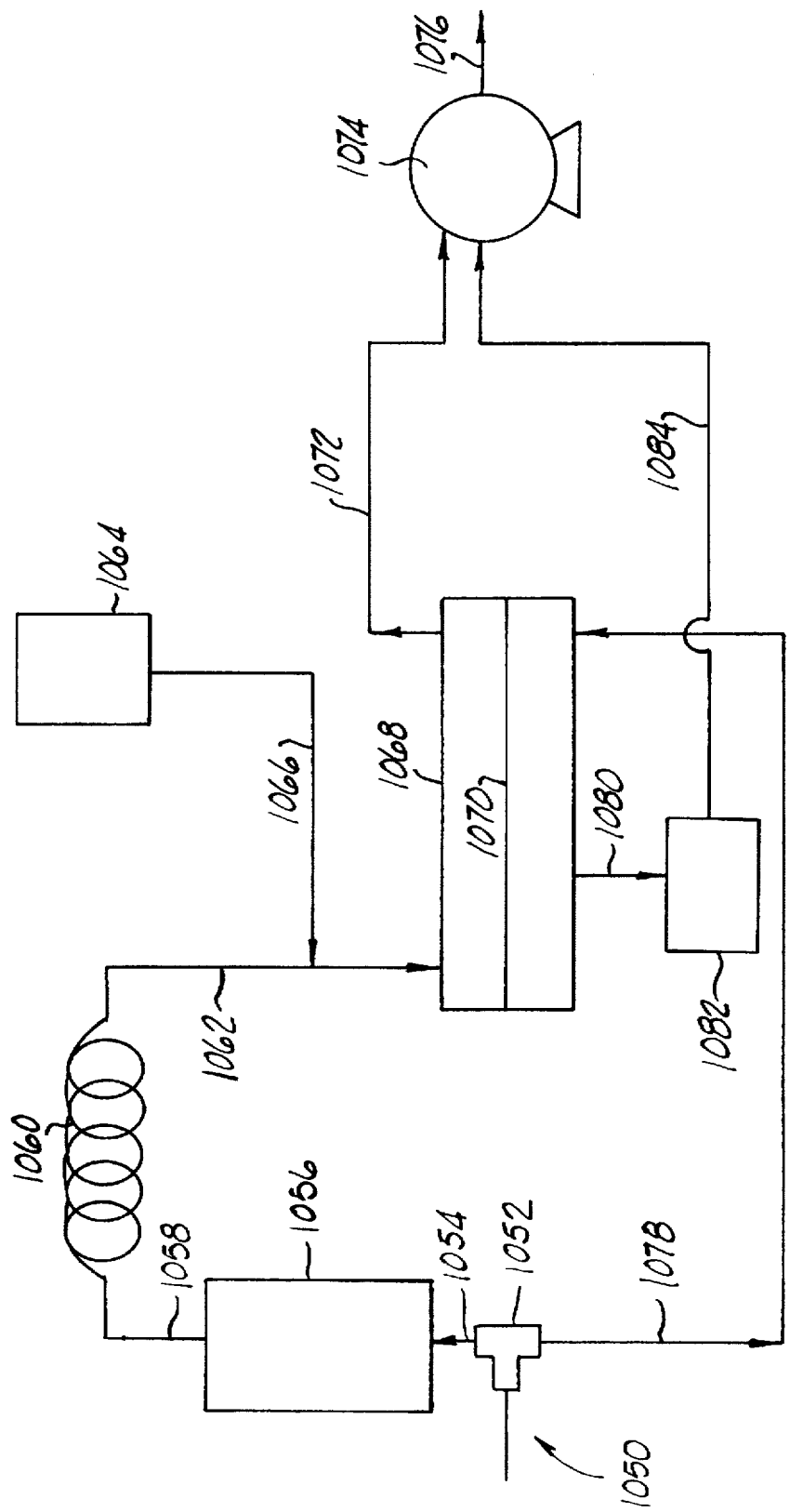
FIG. 6 is a block diagram depicting an alternate embodiment of the present invention wherein a device as in FIG. 1 includes acidification between the oxidation reactor and the gas transfer module.

Further embodiments of the present invention are depicted in FIG. 5 and FIG. 6. The basic configuration of these embodiments is similar to those embodiments depicted in FIG. 4 and FIG. 1 respectively. FIG. 5 includes three temperature and conductivity cells in order to differentiate and measure conductivity associated with heteroorganic impurities. FIG. 5 and FIG. 6 represent improvements over the embodiments of FIG. 4 and FIG. 1, in that means are provided for introducing acid into the first sample stream before it enters the first side of the gas exchange module. According to these embodiments, acid is introduced into the first sample stream to achieve a pH of less than 4.0. By controlling the pH of the first sample stream, it is possible to assure that all of the carbon exiting the oxidation reactor is in the form of carbon dioxide.

Briefly, the embodiment of FIG. 5 includes a sample inlet conduit 1002 that is in communication with a tee fitting 1004 which splits the sample stream into first and second sample streams. Tee fitting 1004 is in communication with conduits 1006 and 1038. Conduit 1006 is in communication with the first temperature and conductivity cell 1008, which is in turn in communication with conduct 1010. Conduit 1010 is in communication with oxidation reactor 1012, which is in turn in communication with conduit 1014, which is also in communication with the inlet to the second temperature and conductivity cell 1016. Conduit 1018 is in communication with the outlet of the second temperature and conductivity cell 1016 and the inlet of the first side of the gas exchange module 1024.

Acidification means 1020 are included in this embodiment of the invention. The acidification means can consist of any type of mechanism for introducing an aqueous inorganic acid into the first sample stream. In one embodiment of the invention, the acidification means 1020 consists of a reservoir that contains the aqueous acid solution, a syringe pump to precisely meter the acid delivery, and means for recharging the syringe pump with the acid from the reservoir. The acidification means 1020 are in communication with conduit 1022, which is in communication with conduit 1018. The gas exchange module 1024 is the same as that described above. Conduit 1040 is in communication with the outlet of the first side of the gas exchange module 1024 and sample outlet 1036.

Conduit 1038 is in communication with the inlet of the second side of the gas exchange module 1024. Conduit 1028 is in communication with the outlet of the second side of the gas exchange membrane 1024, and also with the third temperature and conductivity cell 1030. Conduit 1032 is in communication with the third temperature and conductivity cell 1030 and sample outlet 1036. Flow through both sample streams is generated by pump 1034, preferably a peristaltic pump.

In the embodiment of the invention depicted in FIG. 5, the sample stream exiting the oxidation module is acidified to a pH of 4.0 or lower. By controlling the pH of the first sample stream, the change in pH that is seen when heteroorganic compounds are oxidized to form fully oxidized non-carbon ionic species is reduced or eliminated.

As stated above, FIG. 6 is an improved embodiment of the invention that is essentially identical to the embodiment of FIG. 1. but for the inclusion of acidification means. The embodiment of FIG. 6 includes sample inlet conduit 1050 that is in communication with a tee fitting 1052 which splits the sample stream, and is in communication with conduits 1054 and 1078. Conduit 1054, which contains the first sample stream is in communication with the first temperature and conductivity cell 1056, which is in communication with conduit 1058, which is in communication with the inlet of oxidation reactor 1060. The outlet of the oxidation reactor 1060 is in communication with conduit 1062, which is in communication with the inlet of the first side of the gas exchange module 1068. As in the other embodiments of this invention, the first and second sides of the gas exchange module 1068 are separated by carbon dioxide selective gas permeable membrane 1070.

The acidification means 1064 are in communication via conduit 1066, with conduit 1062. The acidification means 1064 can consist of any means for introducing an aqueous acid solution into the first sample stream as discussed above. The outlet of the first side of the gas exchange module 1068 is in communication with conduit 1072, which is in communication with sample outlet 1076.

Conduit 1078 is in communication with the inlet of the second side of the gas exchange module 1068. Conduit 1080 is in communication with the outlet of the second side of the gas exchange module 1068 and with the second temperature conductivity cell 1082, which is in communication with conduit 1084 which is in communication with sample outlet 1076. Again, flow through both sample streams is controlled by pump 1074.

The embodiment of the TOC detector of the present invention depicted in FIG. 6 is an improved apparatus for the measurement of total organic carbon in deionized water. The provision of acidification means alleviates the errors that are found in the embodiment of FIG. 1 due to the presence of heteroorganic impurities in the sample.

The embodiments of the invention depicted in previous figures are particularly well adapted for the measurement of TOC in deionized water streams. FIG. 7 depicts an embodiment of the present invention that is useful for measuring TOC in non-deionized water—provided that no inorganic carbon is found in the sample streams—or total carbon if the sample stream contains inorganic carbon compounds. The additional elements found in this embodiment are the inclusion of a water deionization module in the second sample stream, and an optional pH meter in the first sample stream.

The embodiment of the TOC detector of the present invention depicted in FIG. 7 comprises a sample inlet conduit 1100, which is communication with a tee fitting 1102, which is in communication with conduits 1104 and 1126. The tee fitting 1102 splits the sample stream into first and second streams. Conduit 1104 is in communication with the first temperature and conductivity cell 1106. Optionally associated with the temperature and conductivity cell 1106 is a pH meter 1108, adapted to monitor the pH of the sample stream. The pH meter can exist at other locations in the apparatus, as long as the sample has not already passed through the oxidation reactor or the water deionization module. The results of the pH meter 1108 are electronically transmitted to the processor section of the apparatus. With the actual pH known of the incoming water, the calculation of carbon in the sample stream is facilitated.

The first temperature and conductivity cell 1106 is in communication with conduit 1110, which is in communication with the inlet of oxidation reaction 1112. Conduit 1114 is in communication with the outlet of oxidation reactor 1112 and the inlet of the first side of the gas exchange module 1116. Conduit 1120 is in association with the outlet of the first side of gas exchange module 1116 and outlet conduit 1124. Conduit 1126 is also in communication with water deionization module 1128. Any water deionization device, well known to those skilled in the art, is acceptable for this application. In the preferred embodiment, the water deionization module 1128 comprises a bed of ion exchange resin (mixed strong base and strong acid). The outlet of water deionization module 1128 is in communication with conduit 1130, which is in communication with the inlet of the second side of gas exchange module 1116. Conduit 1132 is in communication with the outlet of the second side of gas exchange module 1116, and the second temperature and conductivity cell 1134, which is in communication with conduit 1136, which is in turn in communication with sample outlet conduit 1124. Flow through both streams of the apparatus is controlled by pump 1124.

Because of the presence of the water deionization module 1128, the embodiment of FIG. 7 is suitable for the continuous measurement of TOC of non-deionized water sample streams where the sample contains no inorganic carbon. Because inorganic carbons are removed from the second sample stream in the water deionization module, but remain in the first sample stream, not all of the conductivity measured in the second temperature and conductivity cell 1134 will be attributed to carbon dioxide from organic carbon.

Figure 8:
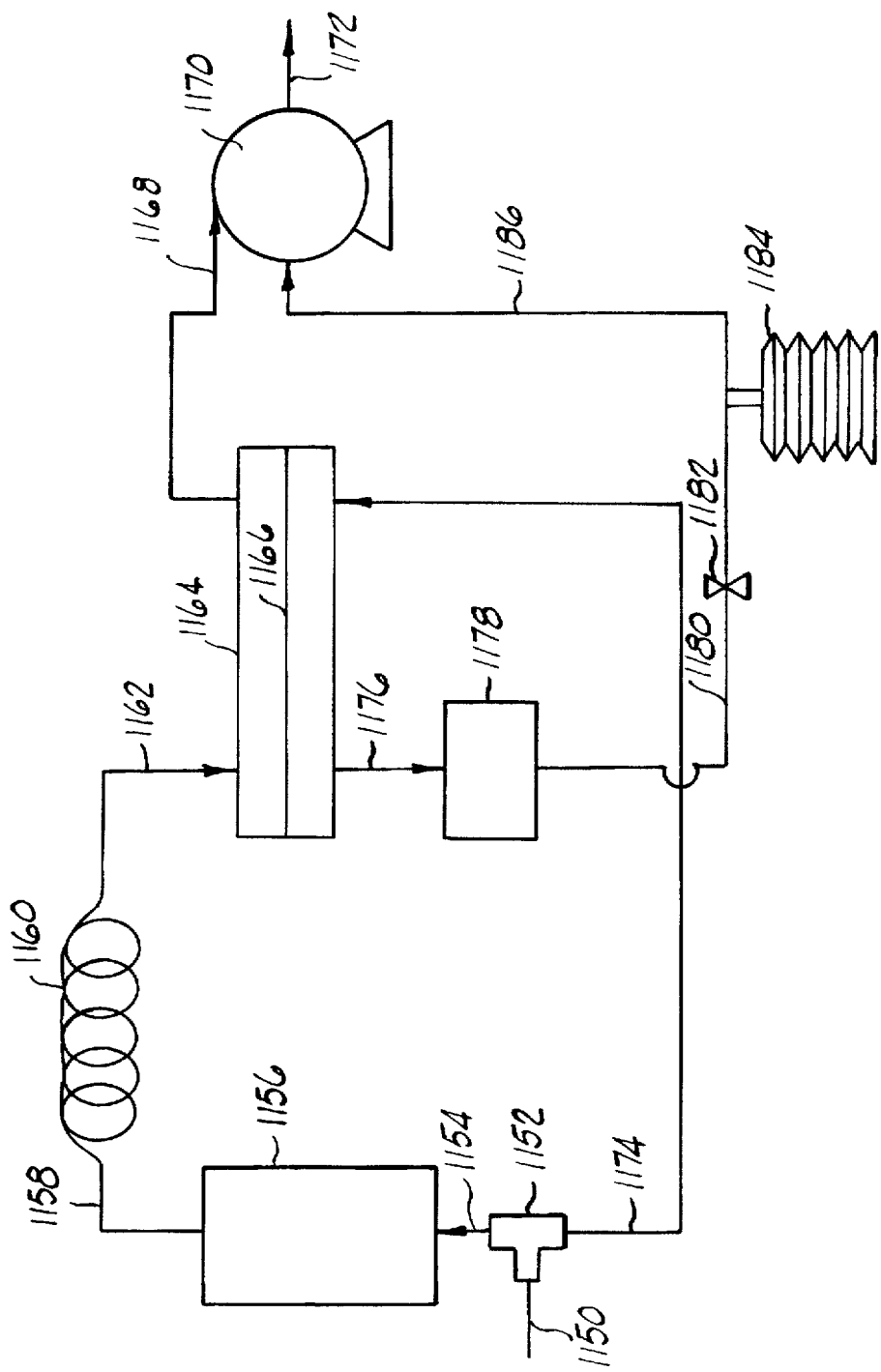
FIG. 8 is a block diagram depicting an alternate embodiment of the present invention wherein the second sample stream flow is pulsed.

In the TOC detector described in U.S. Pat. No. 5,132,094 of Godec, et al., the operation of the gas exchange module operates in a counter-current pulsed mode. The deionized water stream on the second side of the gas permeable membrane is held without flow for a period of time to allow for a more complete transfer of carbon dioxide across the membrane from the continuously flowing oxidized sample stream. The previously described embodiments of the present invention have employed a continuously flowing counter-current system where both first and second streams of sample flow continuously. In an additional alternate embodiment of the present invention, means are included in the sample stream to allow for pulsed flow through the second side of the gas exchange module. A variety of mechanical embodiments can be envisioned in order to adapt the embodiment of FIG. 1 to obtain the pulsed flow. One example is depicted in FIG. 8, where the second sample stream pathway includes a two-way valve and spring loaded bellows. The valve is controlled to open and close according to the predetermined pulsing cycles. The bellows are useful for compensating for the pulsing action and to allow the flow through the second sample stream to be consistent without adjusting the pump speed.

Briefly, FIG. 8 depicts an embodiment of the invention comprising a sample inlet conduit 1150, which is in communication with the tee fitting 1152, which splits the sample stream into first and second streams. Tee fitting 1152 is in communication with conduits 1154 and 1174. Conduit 1154 is in communication with the first temperature and conductivity cell 1156, which is in communication with conduit 1158, which is in communication with the inlet of oxidation reactor 1160. Conduit 1162 is in communication with the outlet of oxidation reactor 1160 and also in communication with the inlet of the first side of gas exchange module 1164. Conduit 1168 is in communication with the outlet of the first side of gas exchange module 1164 and sample outlet 1172.

Conduit 1174 is also in communication with the inlet of the second side of gas exchange module 1164. Conduit 1176 is in communication with the outlet of gas exchange module 1164, and the second temperature and conductivity cell 1178, which is in communication with conduit 1180, which is in communication with two-way valve 1182. The two way valve is solenoid controlled and either allows or prevents flow through conduit 1180 to conduit 1186, which is in communication with sample outlet 1172. Bellows 1184 are also in communication with conduit 1186.

The use of pulsed flow through the second side of the gas exchange membrane increases the sensitivity and linearity of response of the TOC detector of the present invention. In a preferred embodiment, the 2-way valve 1182 and bellows 1184 of FIG. 8 may be replaced with a single solenoid controlled 3-way valve. In the first setting the 3-way valve allows continuous communication between the outlet of the second temperature and conductivity cell 1178 and the sample outlet 1172. In the second setting, flow in the second sample stream is stopped, and ambient air is introduced into the conduit beyond the three way valve.

A final embodiment of the present invention is depicted in FIG. 9. This embodiment is suited for obtaining extremely accurate continuous TOC measurements of non-deionized water sample streams. Similar to the embodiment depicted in FIG. 7, which includes a water deionization module, this embodiment also includes means for removing inorganic carbon from the first sample stream prior to oxidation, and acidification of the first sample stream. This embodiment provides TOC measurements in a manner very similar to the apparatus taught in U.S. Pat. No. 5,132,094.

The TOC detector depicted in FIG. 9 includes a sample inlet conduit 1200, which is in communication with a tee fitting 1202, which is in communication with conduit 1203 and conduit 1228. Conduit 1203 is in communication with optional first temperature and conductivity cell 1204, which is in communication with conduit 1206. Acidification means 1210 are also in communication with conduit 1206 via conduit 1208. Also associated with conduit 1206 are inorganic carbon removal means 1212. In the preferred embodiment, the inorganic carbon removal means 1212 consist of a vacuum degassing module. The inorganic carbon removal means 1212 must be downstream from the introduction of conduit 1208 into conduit 1206.

Conduit 1206 is also in communication with the inlet of oxidation reactor 1214. Conduit 1216 is in communication with the outlet of oxidation reactor 1214 and the inlet of the first side of gas exchange module 1218. Conduit 1222 is in communication with the outlet of the first side of gas exchange membrane 1218 and sample outlet 1226.

Conduit 1228 is in communication with water deionization module 1230, which is in communication with conduit 1232, which is in communication with optional second temperature and conductivity cell 1234. Conduit 1236 is in communication with optional second temperature and conductivity cell 1234 and the inlet of the second side of gas exchange module 1218. The outlet of the second side of gas exchange module 1218 is in communication with third temperature and conductivity cell 1240 via conduit 1238. The third temperature and conductivity cell 1240 is in communication with conduit 1242, which is in communication with outlet conduit 1226. Flow through both first and second streams is induced by pump 1224.

In the embodiment of FIG. 9, the first sample stream is acidified and degassed to remove inorganic carbon prior to oxidation. Therefore, the stream entering the first side of the gas exchange membrane contains carbon dioxide derived purely from the oxidation of organic carbon. The optional first temperature and conductivity cell 1204 provides a baseline for the sample prior to acidification and the removal of inorganic carbon species. The optional second temperature and conductivity cell 1234 provides a conductivity measurement of the sample stream after deionization, and—when compared with the conductivity reading obtained from the optional first temperature and conductivity cell 1204—can be used to quantitate total inorganic carbon of the sample stream.

The present invention represents a significant improvement over the methods and apparatus existing for the measurement of total organic carbon and of inorganic carbon, and for the measurement of total carbon content of deionized water samples. The use of a carbon dioxide selective membrane and conductometric detection applied to the measurement of total organic carbon and total inorganic carbon concentrations in aqueous samples offers several advantages: 1) no purge gas, gas/liquid purge apparatus or drying system is required, 2) the conductometric detection system provides excellent long-term calibration stability (over one year between calibrations) and minimal fouling or contamination since the cell is only exposed to carbon dioxide in deionized water, 3) the size of the conductivity cell can be sufficiently small that accurate measurement in samples as small as 0.1 mL can be achieved, 4) conductometric detection provides a large linear dynamic range, typically three to four orders of magnitude greater than other techniques utilized for the measurement of carbon dioxide in aqueous samples, 5) the sensitivity of the carbon dioxide sensing apparatus is substantially better than in other techniques, 6) no acid or ionic chemical regent oxidizers are added, 7) no sample dilution is required, 8) the selective carbon dioxide membrane based sensor minimizes the interference of other acid gases, 9) the use of a thin and low volume gas transfer module minimizes the response times to allow for practical use in real industrial applications, 10) incorrect higher carbon concentration measurements due to the pressure of inorganic intermediate oxidation products are avoided, since such products do not permeate through the selective carbon dioxide gas permeable membrane, and 11) non-ionic organic halogens and heteroorganic compounds can be measured accurately.

What is claimed is:

1. An apparatus for measurement of carbon in a water sample stream, comprising: means for splitting the sample stream into a first set of conduits to contain a first sample stream and a second set of conduits to contain a second sample stream; a first temperature and conductivity cell in communication with the first set of conduits to measure the conductivity of the first sample stream, an oxidation reactor in communication with the first set of conduits to oxidize organic compounds in the first sample stream to carbon dioxide; a gas permeable membrane to divide the first sample stream from the second sample stream and to allow at least a portion of said carbon dioxide to permeate from the first sample stream to the second sample stream; and a second temperature and conductivity cell in communication with the second set of conduits to measure conductivity of the second sample stream, wherein output from at least one of said temperature and conductivity cells is used for said measurement of carbon.

2. The apparatus of claim 1, wherein the oxidation reactor includes an ultraviolet light source to irradiate the first sample stream with ultraviolet light.

3. The apparatus of claim 1, further comprising a sample pump to pump the first sample stream and second sample stream.

4. The apparatus of claim 1, further comprising the gas-permeable membrane having two sides wherein at least one of said two sides has a stream layer less than 0.06 inches thick and less than 1.000 µL in volume.

5. The apparatus of claim 1, wherein the first temperature and conductivity cell and second temperature and conductivity cell each has a volume of less than 500 µL.

6. The apparatus of claim 1, wherein the oxidation reactor is positioned downstream from the first temperature and conductivity cell and is in communication with the first set of conduits.

7. The apparatus of claim 6, further comprising a third temperature and conductivity cell downstream from the oxidation reactor and in communication with the first set of conduits.

8. The apparatus of claim 1, wherein said gas permeable membrane is a carbon dioxide selective membrane.

9. The apparatus of claim 1, wherein said first sample stream and said second sample stream flow in opposite directions relative to each other at the gas permeable membrane.

10. The apparatus of claim 1, further comprising a water deionization module in communication with the second set of conduits.

11. The apparatus of claim 10, wherein said water deionization module is upstream from the gas permeable membrane.

12. The apparatus of claim 1, further comprising means for introducing acid in communication with the first set of conduits.

13. The apparatus of claim 12, wherein the means for introducing acid are downstream from the oxidation reactor.

14. The apparatus of claim 12, wherein the means for introducing acid are upstream from the oxidation reactor.

15. The apparatus of claim 7, further comprising means for introducing acid in communication with the first set of conduits.

16. The apparatus of claim 15, wherein the means for introducing acid are downstream from the third temperature and conductivity cell.

17. The apparatus of claim 1, further comprising means for pulsing the second sample stream.

18. The apparatus of claim 1, further comprising means for removing inorganic carbon compounds from the first sample stream at a location in said first set of conduits which is upstream from the oxidation reactor.

19. The apparatus of claim 18, further comprising a water deionization module in communication with the second set of conduits.

20. The apparatus of claim 19, wherein the water deionization module is upstream from the gas permeable membrane.

21. An apparatus for measurement of carbon in a water sample stream comprising: means for splitting the sample stream into a first set of conduits to contain a first sample stream and a second set of conduits to contain a second sample stream; a first temperature and conductivity cell in communication with the first set of conduits to measure conductivity of the first sample stream; an oxidation reactor downstream of said first temperature and conductivity cell and in communication with the first set of conduits to oxidize organic compounds in the first sample stream to carbon dioxide; a second temperature and conductivity cell downstream from said oxidation reactor and in communication with the first set of conduits to measure conductivity of the first sample stream downstream from the oxidation reactor; a gas permeable membrane to divide the first sample stream from the second sample stream to the second sample stream; and a third temperature and conductivity cell in communication with the second set of conduits to measure conductivity of the second sample stream downstream of said gas permeable membrane, wherein output from at least one of said temperature and conductivity cells is used for said measurement of carbon.

22. The apparatus of claim 21, wherein the oxidation reactor includes an ultraviolet light source to irradiate the first sample stream with ultraviolet light.

23. The apparatus of claim 21, further comprising a sample pump to pump the first and second sample streams.

24. The apparatus of claim 21, wherein the gas permeable membrane is a carbon dioxide selective membrane.

25. An apparatus for measurement of carbon in a water sample stream comprising: means for splitting the same stream into a first set of conduits to contain a first sample stream and a second set of conduits to contain a second sample stream; a first temperature and conductivity cell in communication with the first set of conduits to measure conductivity of the first sample stream; an oxidation reactor downstream from said first temperature and conductivity cell and in communication with the first set of conduits to oxidize organic compounds in the first sample stream to carbon dioxide; a second temperature and conductivity cell downstream from said oxidation reactor and in communication with the first set of conduits to measure conductivity of the first sample stream downstream from the oxidation reactor; acidification means for introducing acid into the first sample stream at a location downstream from the second temperature and conductivity cell; a gas permeable membrane to divide the first sample stream from the second sample stream and to allow at least a portion of said carbon dioxide to permeate from the first sample stream to the second sample stream; and a third temperature and conductivity cell in communication with the second set of conduits to measure conductivity of the second sample stream, wherein output from at least one of said temperture and conductivity cells is used for said measurement of carbon.

26. The apparatus of claim 25, wherein the oxidation reactor includes an ultraviolet light source to irradiate the first sample stream with ultraviolet light.

27. The apparatus of claim 25, further comprising a sample pump to pump the first and second sample streams.

28. The apparatus of claim 25, wherein the gas permeable membrane is a carbon dioxide selective membrane.

29. An apparatus for measurement of carbon in a water sample stream comprising: means for splitting the sample stream into a first set of conduits to contain a first sample stream and a second set of conduits to contain a second sample stream; a first temperature and conductivity cell in communication with the first set of conduits to measure conductivity of the first sample stream; an oxidation reactor in communication with the first set of conduits to oxidize organic compounds in the first sample stream to carbon dioxide; acidification means for introducing acid into the first sample stream at a location downstream from the oxidation reactor; a gas permeable membrane to divide the first sample stream from the second sample stream and to allow at least a portion of said carbon dioxide to permeate from the first sample stream to the second sample stream; and a second temperature and conductivity cell in communication with the second set of conduits to measure conductivity of the second sample stream, wherein output from least one of said temperature and conductivity cells is used for said measurement of carbon.

30. The apparatus of claim 29, wherein the oxidation reactor includes an ultraviolet light source to irradiate the first sample stream with ultraviolet light.

31. The apparatus of claim 29, further comprising a sample pump to pump the first and second sample streams.

32. The apparatus of claim 29, wherein the gas permeable membrane is a carbon dioxide selective membrane.

33. An apparatus for measurement of carbon in a water sample stream, comprising: means for splitting the sample stream into a first set of conduits to contain a first sample stream and a second set of conduits to contain a second sample stream; a first temperature and conductivity cell in communication with the first set of conduits to measure conductivity of the first sample stream; an oxidation reactor in communication with the first set of conduits to oxidize organic compounds in the first sample stream to carbon dioxide; a gas permeable membrane to divide the first sample stream from the second sample stream and to allow at least a portion of said carbon dioxide to permeate from the first sample stream to the second sample stream; a water deionization module in communication with the second set of conduits for removing ionic compounds from the second sample stream; and a second temperature and conductivity cell in communication with the second set of conduits to measure conductivity of the second sample stream, wherein output from at least one of said temperature conductivity cells is used for said measurement of carbon.

34. The apparatus of claim 33; wherein the oxidation reactor includes an ultraviolet light source to irradiate the first sample stream with ultraviolet light.

35. The apparatus of claim 33, further comprising a sample pump to pump the first and second sample streams.

36. The apparatus of claim 33, wherein the gas permeable membrane is a carbon dioxide selective membrane.

37. An apparatus for measurement of carbon in a water sample stream comprising: means for splitting the sample stream into a first set of conduits to contain a first sample stream and a second set of conduits to contain a second sample stream; a first temperature and conductivity cell in communication with the first set of conduits to measure conductivity of the first sample stream; an oxidation reactor in communication with the first set of conduits to oxidize organic compounds in the first sample stream to carbon dioxide; a gas permeable membrane to divide the first sample stream from the second sample stream and to allow at least a portion of said carbon dioxide to permeate from the first sample stream to the second sample stream; and a second temperature and conductivity cell in communication with the second set of conduits to measure conductivity of the second sample stream; and means for pulsing the second sample stream, wherein output from at least one of said temperture and conductivity cells is used for said measurement of carbon.

38. The apparatus of claim 37, wherein the oxidation reactor includes an ultraviolet light source to irradiate the first sample stream with ultraviolet light.

39. The apparatus of claim 37, further comprising a sample pump to pump the first and second sample streams.

40. The apparatus of claim 37, wherein the gas permeable membrane in a carbon dioxide selective membrane.

41. An apparatus for measurement of carbon in a water sample stream, comprising: means for splitting the sample stream into a first set of conduits to contain a first sample stream and a second set of conduits to contain a second sample stream; means for removing inorganic carbon compounds in the first sample stream in communication with the first set of conduits; an oxidation reactor in communication with the first set of conduits to oxidize organic compounds in the first sample stream to carbon dioxide; a gas permeable membrane to divide the first sample stream from the second sample stream and to allow at least a portion of said carbon dioxide to permeate from the first sample stream to the second sample stream; a water deionization module in communication with the second set of conduits for removing ionic compounds from the second sample stream; and a first temperature and conductivity cell in communication with the second set of conduits to measure conductivity of the second sample stream, wherein output from said temperature and conductivity cell is used for said measurement of carbon.

42. The apparatus of claim 41, further comprising means for introducing acid into the first set of conduits downstream from the oxidation reactor.

43. The apparatus of claim 41, further comprising a second temperature and conductivity cell in communication with the first set of conduits to measure conductivity of the first sample stream.

44. The apparatus of claim 41, further comprising a second temperature and conductivity cell in communication with the second set of conduits to measure the conductivity of the second sample stream wherein said second temperature and conductivity cell is located downstream from the water deionization module, and said first temperature and conductivity cell is located downstream from the gas permeable membrane.

45. The apparatus of claim 41, wherein said means for removing inorganic compounds comprises an acidification means for introducing acid into the first sample stream, and vacuum means for degassing the first sample stream downstream from the acidification means.

46. The apparatus of claim 41, wherein the oxidation reactor includes an ultraviolet light source to irradiate the first sample stream with ultraviolet light.

47. The apparatus of claim 41, further comprising a sample pump to pump the first and second sample streams.

48. The apparatus of claim 41, wherein the gas permeable membrane is a carbon dioxide selective membrane.

49. An apparatus for measurement of carbon in water having an electrical conductivity, said apparatus comprising: means for passing a first portion of said water into a first set of conduits as a first stream and for passing a second portion of said water into a second set of conduits as a second stream; oxidation reactor means in communication with said fist set of conduits of oxidize organic compounds in said first stream to carbon dioxide and form a first stream reactor effluent; a gas permeable membrane separating said second stream from said first stream reactor effluent, said membrane allowing at least a portion of said carbon dioxide to permeate from said first stream reactor effluent through said membrane to said second stream, said membrane having two sides, wherein at last one of said two sides has a stream layer less than 0.06 inch thick and less than 1000 microliters in volume; and a first means for measuring electrical conductivity of said second stream, said first means located downstream from said gas permeable membrane, wherein said electrical conductivity of said second stream is used for said measurement of carbon.

50. The apparatus of claim 49, wherein the oxidation reactor means includes an ultraviolet light source to irradiate said first stream with ultraviolet light.

51. The apparatus of claim 49, further comprising a second means for measuring an electrical conductivity of a said second stream, said second means located upstream from said gas permeable membrane.

52. An apparatus for measurement of carbon in a water sample stream, comprising: means for splitting the sample stream into a first set of conduits to contain a first sample stream and a second set of conduits to contain a second sample stream; an oxidation reactor in communication with the first set of conduits to oxidize organic compounds in the first sample stream to carbon dioxide; a gas permeable membrane to divide the first sample stream from the second sample stream and to allow at least a portion of said carbon dioxide to permeate from the first sample stream to the second sample stream; a first temperature and conductivity cell in communication with said second set of conduits to measure conductivity of the second sample stream upstream from said gas permeable membrane; and a second temperature and conductivity cell in communication with said second set of conduits to measure conductivity of the second sample stream downstream from said gas permeable membrane, wherein output from at least one of said temperature and conductivity cells is used for said measurement of carbon.

53. The apparatus of claim 52, wherein the oxidation reactor includes an ultraviolet light source to irradiate said first sample stream with ultraviolet light.

* * * * *